US009320459B2

(12) United States Patent
Chin et al.

(10) Patent No.: US 9,320,459 B2
(45) Date of Patent: Apr. 26, 2016

(54) GRAVITY-DROP SAFETY HOLDER

(75) Inventors: Sin Fong Chin, Singapore (SG); Chee Leong Alvin Tan, Singapore (SG); Yaohan Jon Moh, Singapore (SG); Kiat Jin Cheng, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1701 days.

(21) Appl. No.: 11/429,808

(22) Filed: May 8, 2006

(65) Prior Publication Data
US 2007/0260193 A1 Nov. 8, 2007

(51) Int. Cl.
*A61B 5/15* (2006.01)
*A61M 5/32* (2006.01)

(52) U.S. Cl.
CPC .......... *A61B 5/1444* (2013.01); *A61B 5/1405* (2013.01); *A61B 5/1433* (2013.01); *A61M 5/322* (2013.01); *A61M 5/3232* (2013.01); *A61M 5/3273* (2013.01); *A61M 2005/3217* (2013.01); *A61M 2005/3226* (2013.01)

(58) Field of Classification Search
CPC .. A61B 5/1405; A61B 5/1433; A61B 5/1444; A61M 5/3271; A61M 5/3273; A61M 2005/3217; A61M 5/322; A61M 2005/3226; A61M 5/3232
USPC ............ 604/3, 243, 110, 232, 192–198, 263; 600/576–579
See application file for complete search history.

(56) References Cited

U.S. PATENT DOCUMENTS

| 4,927,414 | A | | 5/1990 | Kulli | |
|---|---|---|---|---|---|
| 4,942,881 | A | | 7/1990 | Al-Sioufi et al. | |
| 4,984,580 | A | | 1/1991 | Wanamaker | |
| 5,030,209 | A | * | 7/1991 | Wanderer et al. | 604/198 |
| 5,117,837 | A | | 6/1992 | Wanamaker et al. | |
| 5,143,083 | A | | 9/1992 | Al-Sioufi et al. | |
| 5,299,687 | A | | 4/1994 | Hanifl et al. | |
| 5,605,544 | A | | 2/1997 | Tsao | |
| 5,709,669 | A | * | 1/1998 | Haining | 604/232 |
| 5,755,673 | A | * | 5/1998 | Kinsey | 600/577 |
| 5,769,826 | A | * | 6/1998 | Johnson et al. | 604/195 |
| 5,810,775 | A | * | 9/1998 | Shaw | 604/110 |
| 5,836,917 | A | * | 11/1998 | Thorne et al. | 604/164.11 |

(Continued)

FOREIGN PATENT DOCUMENTS

| DE | 10348603 | 5/2005 |
|---|---|---|
| DE | 202005013182 | 12/2005 |

(Continued)

*Primary Examiner* — Matthew F DeSanto
(74) *Attorney, Agent, or Firm* — The Webb Law Firm

(57) ABSTRACT

A safety blood collection device including holder housing adapted to maintain a needle cannula with a puncture tip extending from a forward end thereof and to receive a sample collection tube through a rearward end thereof. A retainer coacts with the holder housing to maintain the needle in a first position with the puncture tip of the needle extending from the forward end of the holder housing. The retainer is adapted for activation so as to release the needle from this first position, thereby permitting the needle to move based on the force of gravity and the weight of the needle to a second position in which the puncture tip of the needle cannula is contained within the interior chamber of the holder housing. As such, upright placement of the holder housing upon activation of the retainer will permit the needle to drop within the holder housing, thereby containing the needle cannula therein as a self-contained assembly.

24 Claims, 21 Drawing Sheets

(56) References Cited

U.S. PATENT DOCUMENTS

| | | | |
|---|---|---|---|
| 5,951,515 A * | 9/1999 | Osterlind | 604/110 |
| 6,093,170 A * | 7/2000 | Hsu et al. | 604/110 |
| 6,152,901 A * | 11/2000 | Arruego et al. | 604/195 |
| 6,306,118 B1 * | 10/2001 | Crawford et al. | 604/243 |
| RE37,908 E * | 11/2002 | Kinsey | 600/577 |
| 6,595,931 B2 * | 7/2003 | Ranford | 600/573 |
| 6,764,465 B2 * | 7/2004 | Chen | 604/110 |
| RE39,107 E * | 5/2006 | Shaw | 604/110 |
| 2003/0040717 A1 | 2/2003 | Saulenas et al. | |
| 2003/0093009 A1 | 5/2003 | Newby et al. | |
| 2005/0085745 A1 * | 4/2005 | Kitta et al. | 600/576 |
| 2007/0123821 A1 * | 5/2007 | Wang et al. | 604/110 |

FOREIGN PATENT DOCUMENTS

| | | | |
|---|---|---|---|
| DE | 202005013182 U | * | 12/2005 |
| EP | 1506740 A1 | | 2/2005 |

* cited by examiner

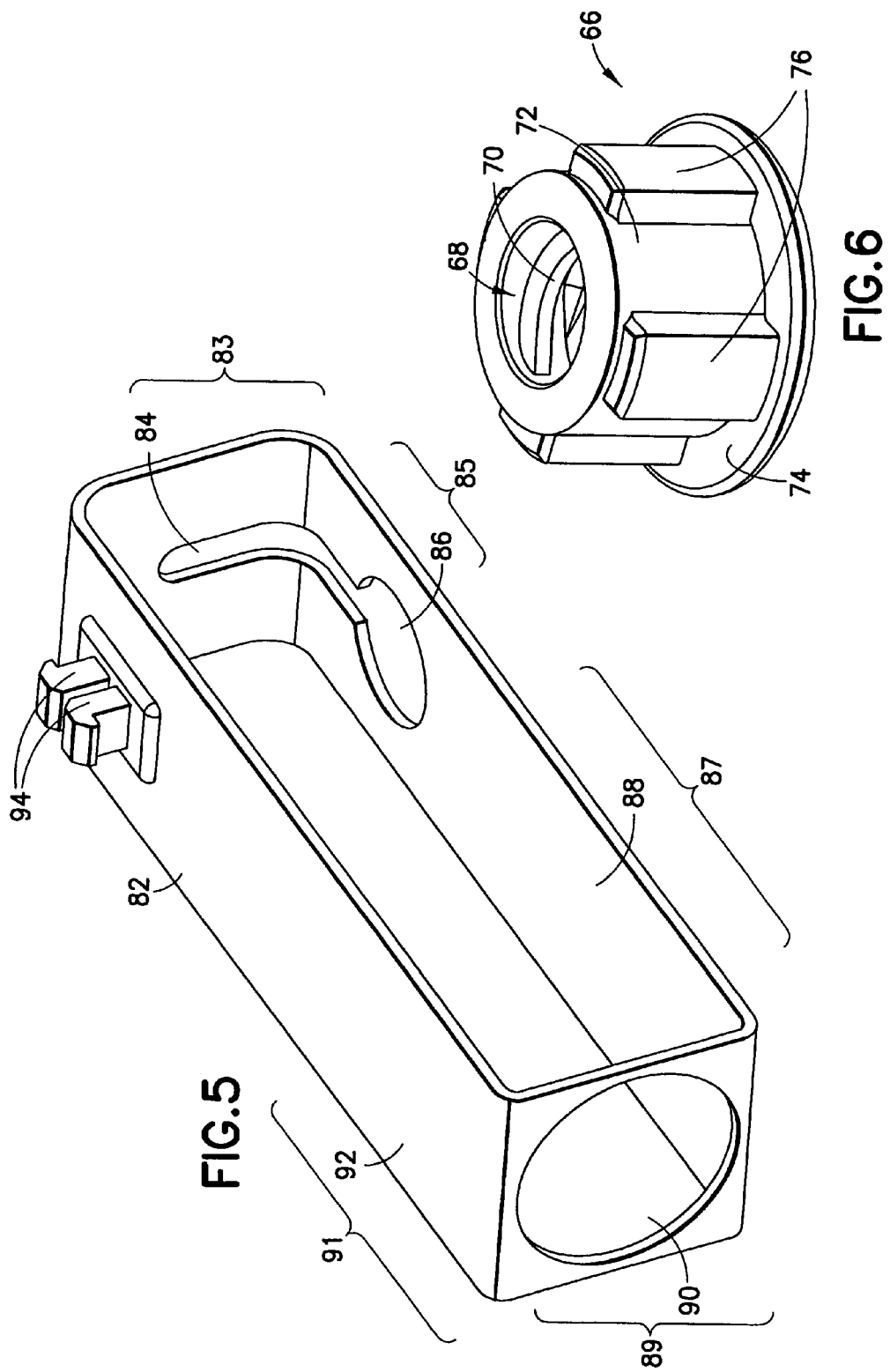

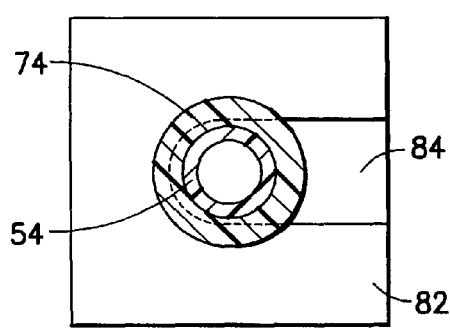
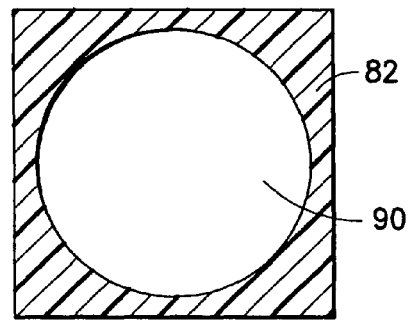
FIG.7B                FIG.7C
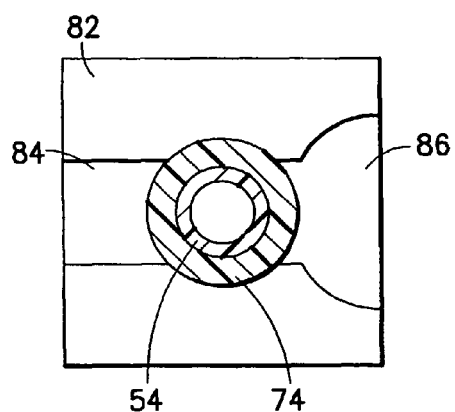
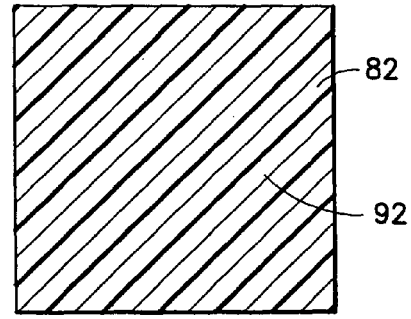
FIG.8B                FIG.8C

GRAVITY-DROP SAFETY HOLDER

BACKGROUND OF THE INVENTION

1. Field of the Invention

The present invention relates to a blood collection assembly having safety elements for safe and convenient handling. More particularly, the present invention relates to a blood collection assembly which is adapted for retraction of the needle based on forces of gravity.

2. Description of Related Art

Disposable medical devices having piercing elements are typically used for administering a medication to or withdrawing a fluid from a patient, such as blood collecting needles, fluid handling needles and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after use.

A popular design configuration of conventional blood collection systems includes a double-ended needle assembly, an evacuated collection tube, and a holder for maintaining the needle assembly and the collection tube in fixed relation. The double-ended needle assembly has a bore extending through a cannula and a hub near a central region thereof. The evacuated fluid collection tube includes a puncturable stopper at one end thereof. In this type of blood collection system, the holder typically has a housing at one end thereof for receiving the needle assembly. Likewise, the holder also has a hollow body with an opening at an opposite end thereof for receiving the collection tube. The needle assembly is rigidly received within the housing of the holder such that a first end of the needle, i.e., the patient end, extends forwardly of the holder for puncturing a vein of a patient. The opposite, second end of the needle, i.e., the non-patient end, extends into the hollow body of the holder. Upon assembly of the blood collection system, the needle assembly is inserted into the housing and the collection tube is inserted through the open end of the hollow body until the second end of the needle pierces the puncturable stopper of the collection tube, thereby allowing fluid communication between the interior of the collection tube and the bore which extends through the needle assembly. To draw a blood specimen from a patient using one of these blood collection systems, the evacuated collection tube is partially inserted into one end of the holder, the first end of the needle is inserted into a patient's vein, and the collection tube is fully inserted into the holder such that blood will be drawn through the bore of the needle assembly and into the fluid collection tube. After drawing the specimen, the collection tube is removed so that the blood contained therein can be analyzed and the needle assembly is detached for disposal.

In addition to being capable of accommodating blood collection tubes, the holders of some fluid transfer systems are compatible with fluid containers having a fluid to be injected into a patient. Thus, such holders can be used to inject fluid into, as well as draw blood specimens from, a patient.

Traditionally, needle holders for such blood collection assemblies have been re-usable, with the needle assembly detached from the needle holder after use, and a new needle assembly attached to the needle holder for re-use thereof, often for use with a new patient. For example, U.S. Pat. No. 6,306,118 discloses a needle holder assembly for use with a separate double-ended blood collection needle which can be easily engaged to and disengaged from the holder through a trigger arrangement, providing for release of the needle from the holder and into a separate sharps container. Similar needle holders which are adapted for quick release and separation of the needle from the needle holder into a separate container are disclosed in U.S. Pat. Nos. 4,942,881; 4,984,580; 5,117,837; 5,143,083; 5,299,687; and 5,755,673. Re-use of a needle holder with different needle assemblies provides the possibility of contamination, such as blood spatter within the needle holder.

Moreover, in order to reduce the risk of incurring an accidental needle-stick wound, protection of the used needle tip becomes important. With concern about infection and transmission of diseases, methods and devices to enclose the used disposable needle have become very important and in great demand. Arrangements have been designed for protecting used needle tips involving retracting the needle within the needle holder with the entire device including the needle holder and the needle assembly being disposed of together. For example, U.S. Pat. No. 5,810,775 to Shaw discloses a collection assembly which provides for retraction of the intravenous needle at the patient end of the assembly, and further discloses a hinged cap at the open end of the housing of the holder. After drawing a specimen into a collection tube, the collection tube is removed, and the hinged cap is closed over the opening of the holder, thereby activating the spring-based needle retraction and blocking access to the second end of the needle at the non-patient end. Activation of the hinged cap and the spring-based retraction mechanism requires substantial manipulation by the user and cannot be conveniently accomplished with a single hand, as is ideal for typical phlebotomy practice.

U.S. Patent Application Publication No. 2003/0040717 discloses a retracting needle safety device in which a retraction assembly including a double-ended needle cannula with a patient tip at one end and a non-patient tip at an opposed end is retracted within a tubular body of a needle holder housing after use. The retraction is accomplished through a spring mechanism which biases the retraction assembly into the body of the needle holder housing to contain the needle entirely therein in a manner which is offset from the general axis of the housing.

U.S. Patent Application Publication No. 2003/0093009 also discloses a needle safety device with a double-ended needle cannula having a patient tip at one end and a non-patient tip at an opposed end, with the needle cannula permanently mounted to a housing for accommodating an evacuated blood collection tube. A spring propels a safety shield to a shielding position covering the patient tip of the needle cannula upon activation, which is accomplished passively when a tube is inserted within the housing by the tube contacting a latch which releases the shield.

Such prior art retractable needle assemblies and releasable needle assemblies include complex mechanisms for activation, with many relying on spring biasing forces for forced retraction into the attached needle holder housing, or for separation from the housing into a separate container for storing of used needles or sharps.

SUMMARY OF THE INVENTION

A need exists for a self-contained needle assembly which provides effective protection from both ends of a double-ended needle with simple and efficient retraction of the needle, and which is simple to manufacture and easy to operate.

A safety blood collection device comprises a holder housing including a generally tubular wall extending between a forward end and an open rearward end to define an interior chamber therein, with the rearward end of the holder housing adapted to receive a sample collection tube therethrough and a needle including a puncture tip extending from the forward end of the holder housing. A retainer co-acts with the holder housing to maintain the needle in a first position with the puncture tip of the needle extending from the forward end of the holder housing. The retainer is adapted for activation so as to release the needle from this first position, thereby permitting the needle to move based on the force of gravity to a second position in which the puncture tip of the needle is contained within the interior chamber of the holder housing. As such, upright placement of the holder housing upon activation of the retainer will permit the needle to drop within the holder housing, thereby containing the needle cannula therein.

The needle may comprise a needle hub including a needle cannula, which may be a double-ended needle cannula including a first end having the puncture tip extending from a forward end of the hub, and a second end having a non-patient puncture tip extending from a rearward end of the hub for engagement with a sample collection tube received through the rearward end of the holder housing with the retainer maintaining the needle hub in the first position.

Desirably, the retainer includes structure for establishing interference engagement for maintaining the needle in the first position with the puncture tip extending from the forward end of the holder housing. The retainer may be adapted to move upon activation thereof, such that movement of the retainer from a first position to a second position causes release of the interference engagement, thereby permitting the needle to move to the second position, i.e., drop within the interior chamber of the holder housing. The assembly may further include structure adapted to close the rearward end of the holder housing when the retainer is in the second position, so as to prevent access to the interior chamber through the rearward end, thereby preventing contact with the needle contained therein.

A separate hub port may be provided adjacent the forward end of the holder housing for interconnecting the needle hub with the holder housing, such as through a threaded engagement between the needle hub and the hub port. In such an embodiment, the retainer may include structure in interference engagement with the hub port to prevent the needle hub from being released from the forward end of the housing and to maintain the needle hub in the first position with the puncture tip extending from the forward end of the housing. Movement of the retainer to the second position releases the interference engagement between the retainer and the hub port, thereby releasing the hub port and the needle hub and permitting movement of the needle to the second position.

In one particular embodiment, the retainer comprises a flexible band member including a first portion having a slot which is positioned adjacent the forward end of the holder housing when the flexible band member is in the first position. The needle hub is maintained in a position extending from the forward end of the holder housing in interference engagement with the slot. Movement of the flexible band member toward the second position aligns the needle hub with a second portion of the flexible band member including an opening, which releases the interference engagement, to permit the needle hub to pass through the opening to the second position in which the puncture tip of the needle cannula is contained within the interior chamber of the holder housing. The flexible band member may further include a third portion, such as a solid flap, adapted to enclose the forward end of the holder housing when the flexible band member is in the second position to prevent re-exposure of the puncture tip of the needle cannula therethrough. Also, the flexible band member may include an opening which is positioned adjacent the rearward end of the holder housing when the flexible band member is in the first position. Desirably, when the flexible band member is moved to the second position, a further flap portion closes the rearward end of the holder housing to prevent access to the interior chamber through the rearward end. Movement of the flexible band member may be accomplished through a finger tab extending through a portion of the housing. Desirably, the flexible band member comprises a continuous band member movable about an interior perimeter of the holder housing. In such an embodiment, a holder insert may be further provided within the holder housing, with the flexible band member sandwiched between the holder insert and the holder housing and adapted for movement therebetween.

In an alternate embodiment, the retainer comprises a clamping mechanism integrated with the holder housing. In such an embodiment, the clamping mechanism is adapted to move between a first position in which the clamping mechanism secures the needle hub in the first position with the needle cannula extending from the forward end of the holder housing to a second position in which the needle hub is released from the clamping mechanism, thereby permitting the needle hub to move based on the force of gravity to the second position. In this manner, movement of the clamping mechanism to the second position with the holder housing in an upright position permits the needle hub to drop within the holder housing for containment therein. In such an embodiment, the needle hub may further comprise an internal carrier structure extending within the interior chamber of the holder housing. The internal carrier structure prevents movement of the needle hub through the rearward end of the holder housing upon movement of the needle hub to the second position. Such an arrangement is particularly useful with a double-ended needle, in which the needle cannula comprises a first end having a puncture tip extending from a forward end of the needle hub and a second end including a non-patient puncture tip extending from a rearward end of the needle hub. The internal carrier structure desirably extends beyond the length of the non-patient puncture tip within the interior chamber of the holder housing, and includes structure for interference engagement with a portion of the holder housing when the needle hub is in the second position, thereby preventing the non-patient puncture tip from extending through the rearward opening of the holder housing.

In a further alternate embodiment, the retainer comprises a ring structure which is rotatable with respect to the holder housing about a longitudinal axis between a first position and a second position. The ring structure includes a tab in interference engagement with the needle hub for maintaining the needle hub in the first position extending from the forward end of the holder housing when the ring structure is in the first position. Rotation of the ring structure to the second position releases the interference engagement between the tab and the needle hub, thereby permitting the needle hub to move based on the force of gravity to the second position in which the puncture tip of the needle cannula is contained within the interior chamber of the holder housing. Desirably, the ring structure extends about an external surface of the holder housing and includes at least one tab extending through the holder housing for interference engagement with the needle hub. The needle hub may include at least one gap extending about a periphery thereof, such that rotation of the ring structure with respect to the holder housing aligns the at least one tab of the ring structure with the at least one gap of the needle hub. In this manner, the interference engagement between the at least one tab and the needle hub is released, thereby permitting the needle hub to move to the second position based on the force of gravity. The needle hub may further include an internal carrier structure extending within the interior chamber of the holder housing to prevent movement of the needle hub through the rearward end of the holder housing upon movement of the needle hub to the second position.

In yet a further embodiment, a method for containing a needle after use in a blood collection procedure is provided. The method involves providing a blood collection device comprising a holder housing comprising a generally tubular wall extending between a forward end and an open rearward end to define an interior chamber therein, and a needle including a puncture tip maintained in a first position extending from the forward end of the holder housing through a retainer co-acting with the holder housing and including structure in interference engagement with a portion of the needle. In the method, the retainer is activated to release the interference engagement between the retainer and the needle, with the blood collection device positioned such that gravitational forces move the needle to a second position in which the puncture tip of the needle is contained within the interior chamber of the holder housing.

Desirably, the retainer comprises a flexible band member including a slot adjacent the forward end of the holder housing for establishing interference engagement with the needle hub and an opening adjacent the slot. Accordingly, activation of the retainer comprises moving the flexible band member with respect to the holder housing to align the needle with the opening adjacent the slot, thereby releasing the interference engagement between the slot and the needle to allow the needle to pass through the opening during the positioning step.

In a further embodiment, a safety blood collection device comprises a needle extending between a forward end having a patient puncture tip and a rearward end having a non-patient puncture tip; and a needle holder comprising a generally tubular wall extending between a forward end and an open rearward end to define an interior chamber therein. The holder retains the needle in a first position in which the patient puncture tip extends through the forward end of the holder with the non-patient puncture tip maintained within the interior chamber, and is adapted to release the needle from the first position, thereby permitting the needle to move based on the force of gravity to a second position in which the patient puncture tip and the non-patient puncture tip are contained within the interior chamber of the holder. In such an embodiment, the needle holder comprises a retainer adapted to maintain the needle in the first position, with the retainer adapted for activation so as to release the needle from the first position to permit movement to the second position. The needle may be contained and maintained within the interior of the holder after release and movement of the needle from the first position to the second position by structure covering the open rearward end of the needle holder, such as a hinged cover or a rotating flexible band. Alternatively, the needle is contained and maintained within the interior of the holder after release and movement by a carrier structure preventing movement of the needle through the open rearward end of the needle holder upon movement of the needle to the second position.

BRIEF DESCRIPTION OF THE DRAWING(S)

FIG. 5 is a perspective view of a retainer in the form of a flexible band of the device of FIG. 1.

FIG. 6 is a perspective view of a hub port of the device of FIG. 1.

FIG. 7B is a top down view taken alone line 7B-7B of FIG. 7A.

FIG. 7C is a bottom up view taken alone line 7C-7C of FIG. 7A.

FIGS. 8B and 9B are top down views taken alone lines 8B-8B and 9B-9B of FIGS. 8A and 9A, respectively.

FIGS. 8C and 9C are bottom up views taken alone line 8C-8C and 9C-9C of FIGS. 8A and 9A, respectively.

DESCRIPTION OF THE PREFERRED EMBODIMENT(S)

The present invention is generally directed to a safety blood collection device, which allows for safe and convenient retraction of a phlebotomy needle, such as a double-ended needle, into a holder device, providing a self-contained device. Generally speaking, retraction of the needle is accomplished by activating a retainer member on the device, which releases the needle assembly, and permits retraction of the needle assembly into the general cavity or interior opening of the holder device based on forces of gravity. After containment in this manner, the device is safe from accidental needle sticks, which may occur during disposal of a needle in a conventional container.

Figure 1:
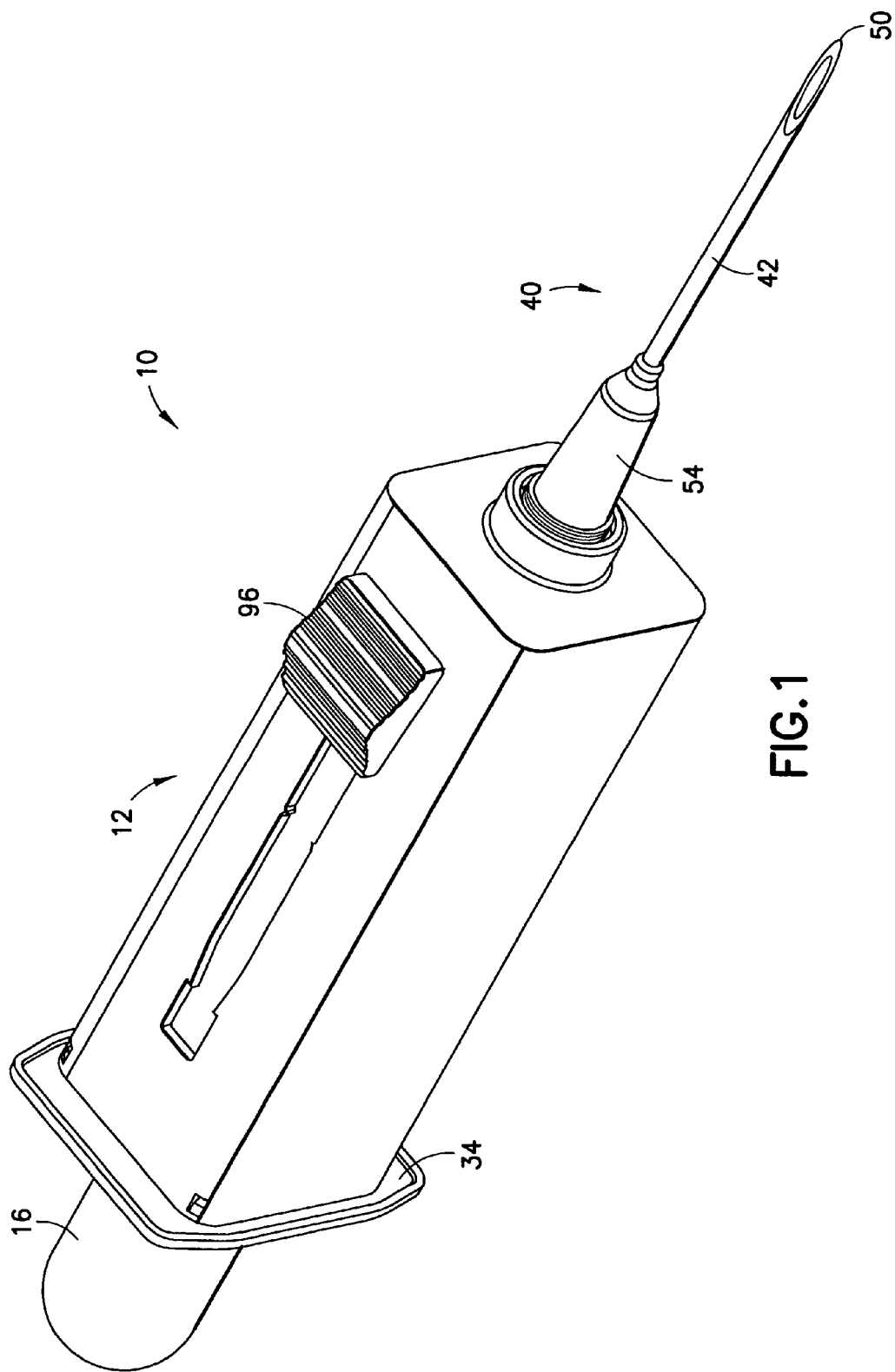
FIG. 1 is a perspective view of a safety blood collection device in accordance with an embodiment of the invention, shown in use with a blood collection tube.
Figure 2:
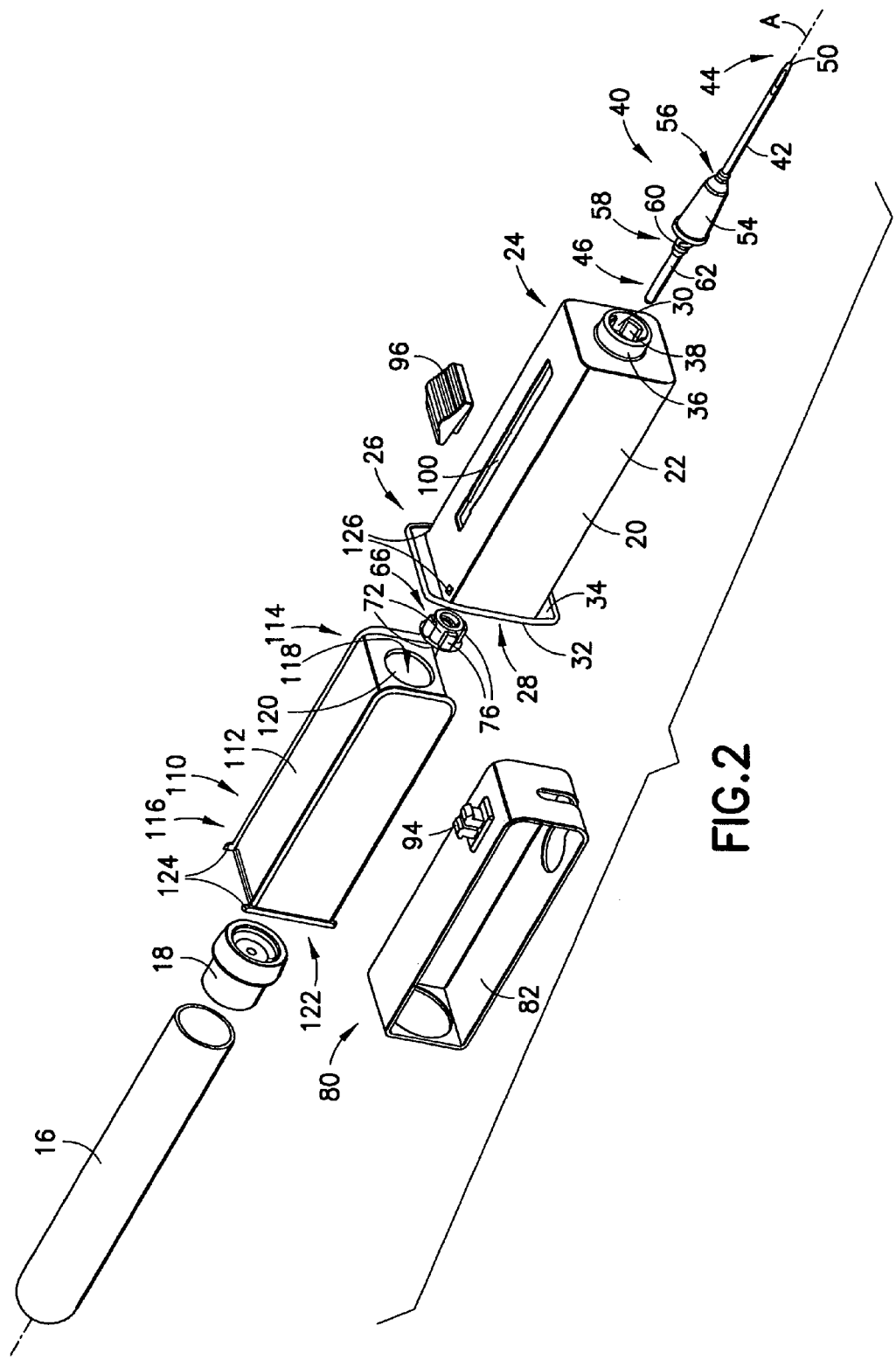
FIG. 2 is an exploded perspective view of the safety blood collection device shown in FIG. 1.
Figure 3:
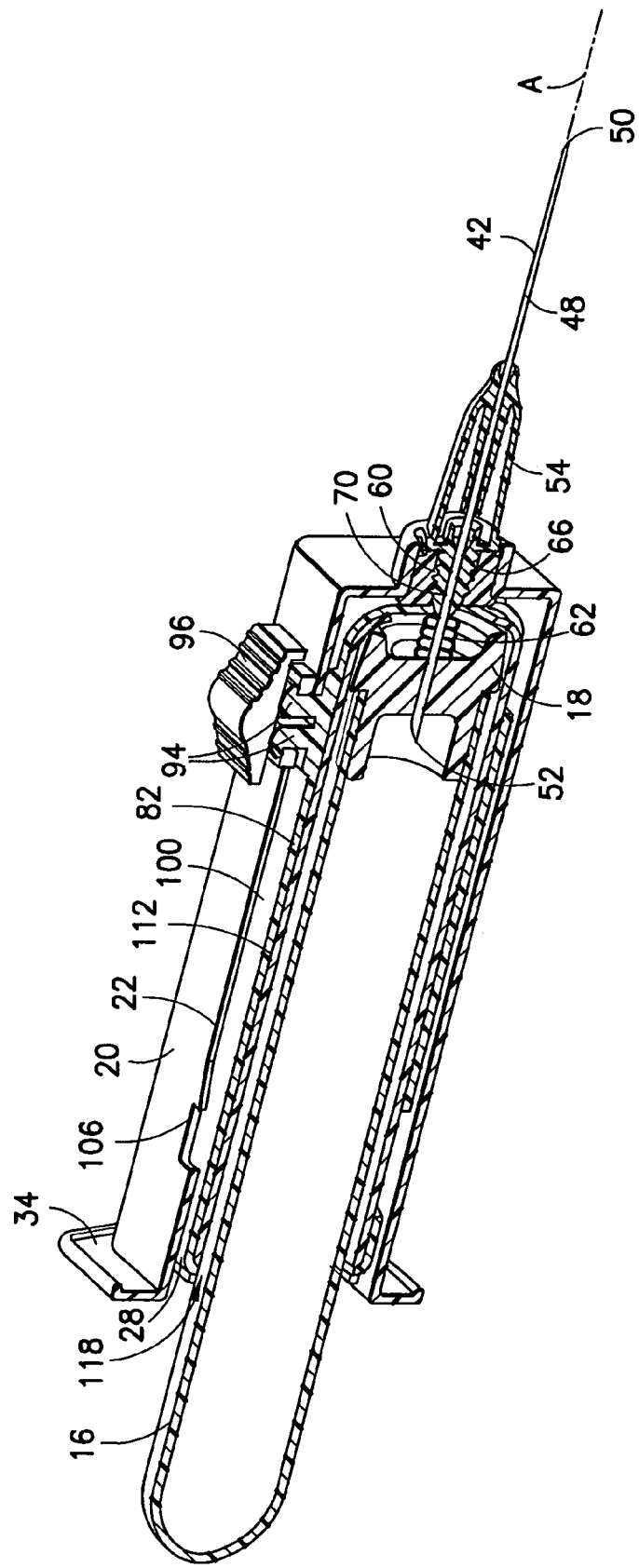
FIG. 3 is a sectional perspective view of the safety blood collection device shown in FIG. 1 in use with the blood collection tube.

Referring to the drawings in which like reference characters refer to like parts throughout the several views thereof, FIGS. 1-3 illustrate a blood collection device 10 in accordance with an embodiment of the present invention and its related features. The blood collection device 10 includes a needle holder 12 in combination with a needle, in particular a needle assembly 14 in the form of a double-ended needle, for use in collecting blood samples with a conventional evacuated blood collection tube 16.

Figure 4:
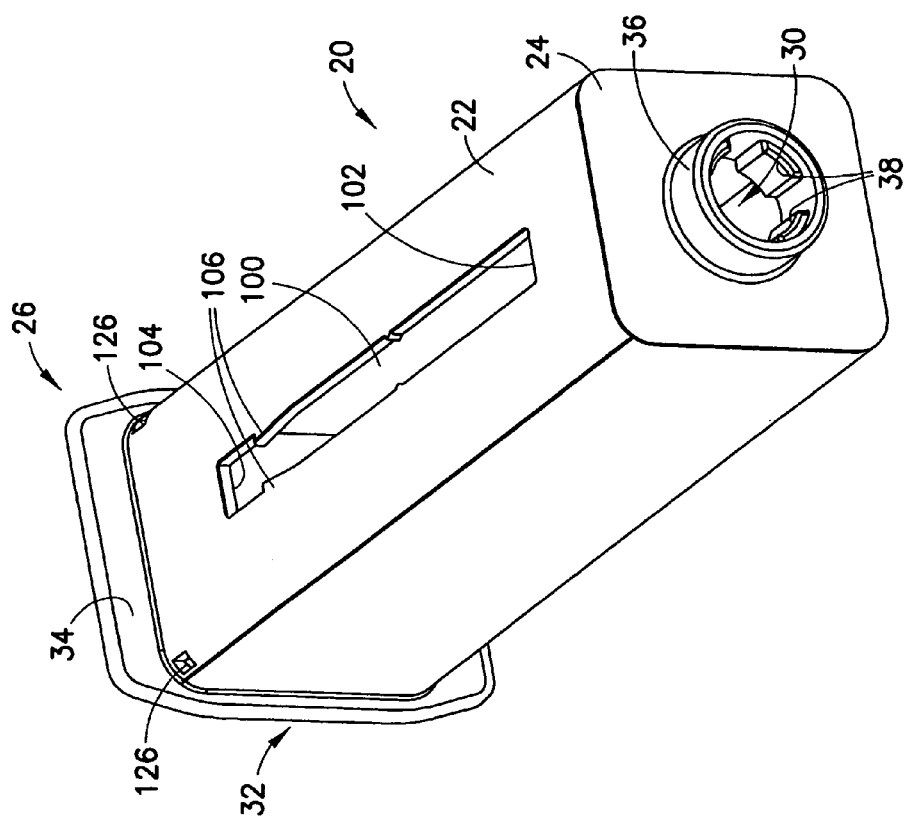
FIG. 4 is a perspective view of a holder housing of the device of FIG. 1.

With particular reference to FIG. 4, holder 12 is defined generally by an outer housing 20 defining a generally hollow tubular wall 22 which includes a first or forward end 24 and a second or rearward end 26, with tubular wall 22 further defining an interior chamber 28 therein. Tubular wall 22 extends along an axis A which generally defines the elongated shape of holder 12, and is generally tubular in form. Tubular wall 22 may be of any cross-sectional profile, and is desirably a non-circular cross-sectional profile, such as a generally square shaped cross-sectional profile as shown. As such, while housing 20 is described as a tubular structure, housing 20 may define any tubular shape, such as a cylindrical tube, a square tube, or any other tubular shape. Forward end 24 of housing 20 includes a forward opening 30 extending therethrough, while rearward end 26 is generally open-ended through rearward opening 32, providing housing 20 as a generally hollow tubular outer body having an interior chamber 28 extending therethrough. Such interior chamber 28 accommodates blood sampling tube 16 during a sampling procedure, as is known in the art. Housing 20 may further include a flange 34 at rearward end 26. Holder 12 may be comprised of moldable parts which can be mass produced from a variety of materials including, for example, polyethylene, polyvinyl chloride, polystyrene or the like.

Blood collection device 10 further includes a needle assembly 40 adapted for assembly with holder 12. Needle assembly 40 generally includes a needle cannula 42 assembled with a needle hub 54. The needle cannula 42 includes a distal or forward end 44 and an opposing proximal or rearward end 46, with a lumen 48 extending through needle cannula 42 between the forward end 44 and the rearward end 46. The forward end 44 of needle cannula 42 may be beveled to define a sharp puncture tip 50, such as an intravenous puncture tip 50. The puncture tip 50 is provided for insertion into a patient's blood vessel, such as a vein, and is therefore designed to provide ease of insertion and minimal discomfort during venipuncture. The rearward end 46 includes a non-patient puncture tip 52, which is provided for puncturing of an evacuated tube, for example, during a blood collection procedure. Needle cannula 42 is desirably constructed of a medical grade metallic material, such as surgical steel or the like.

Needle assembly 40 further includes a needle hub 54. Hub 54 is generally tubular or cylindrical in shape, and may be a unitary structure, desirably molded from a resilient thermoplastic material, or may be a multi-component structure. Hub 54 includes a distal or forward end 56 and an opposed proximal or rearward end 58. The rearward end 58 of hub 54 includes an external portion or structure for mating with needle holder 12, such as external threads 60, as will be discussed in more detail herein. Needle assembly 40 may further include an elastomeric sleeve 62 extending about non-patient puncture tip 52 of needle cannula 42, as is generally known in the art for double-ended blood collection needles. As such, a standard double-ended needle can be used as needle assembly 40.

Needle cannula 42 and hub 54 may be separate parts that are preferably fixedly attached and secured through an appropriate medical grade adhesive, for example, epoxy or the like. In particular, the needle cannula 42 may extend through the interior of the hub 54 and be supported by the hub 54. For this purpose, the hub 54 defines a passageway or opening extending therethrough for receiving and securing the needle cannula 42 therein, such that forward end 44 of needle cannula 42 extends from the forward end 56 of hub 54 and rearward end 46 of needle cannula 42 extends from the rearward end 58 of hub 54.

Needle holder 12 includes structure for engagement with hub 54 of needle assembly 40 to maintain needle assembly 40 in fixed relation thereto. Hub 54 is not attached directly to holder 12, but instead is indirectly connected to holder 12 through a separate member so as to allow for easy release of the needle assembly 40 with respect to the holder 12 for retraction thereof. For example, a hub port 66 may be provided adjacent the forward end 24 of housing 20. As shown with particular reference to FIG. 6, hub port 66 is desirably a cylindrical member including a main skirt portion 68, depending from a port flange 70. Hub port 66 is adapted for interfitting with forward end 24 of housing 20. For example, outer housing 20 may include a depending skirt 36 extending from the forward end 24 thereof defining forward opening 30. Main skirt portion 68 may extend partially within depending skirt 36 of holder housing 20, providing a location for attachment of needle hub 54 of needle assembly 40 to needle holder 12. The outer diameter of port flange 70 of hub port 66 is slightly greater than the internal diameter of forward opening 30 of outer housing 20, thereby preventing hub port 66 from passing through forward opening 30 when fully assembled.

Hub port 66 includes an internal opening 68 for accommodating needle assembly 40 therein, and includes structure to establish mating engagement between needle assembly 40 and housing 20, such as through a threaded or snap-fit attachment, through permanent bonding, or other connecting manner. For example, hub port 66 may include internal threads 70 provided on an internal surface within internal opening 68 for threaded engagement with external threads 60 provided on an external surface of hub 54. In such an arrangement, hub port 66 may further be provided with structure to prevent rotation of hub port 66 during threading of needle assembly 40 thereto. For example, one or more nubs 72 may be provided about the external surface of hub port 66, such as a plurality of nubs 72 radially spaced about skirt 68. Housing 20 may include a corresponding plurality of nubs 38 extending radially within the internal surface of depending skirt 36 at forward opening 30. Hub port 66 is aligned within depending skirt 36 of housing 20 such that nubs 72 of hub port 66 and nubs 38 within depending skirt 36 provide for interference engagement therebetween, thereby preventing rotative movement of hub port 66, particularly during threading of needle assembly 40 with hub port 66 during assembly thereof. It is further contemplated that needle hub 54 and/or needle cannula 52 may be integrally formed directly with hub port 66.

Blood collection device 10 further includes a mechanism to maintain needle assembly 40 in a first position extending from the forward end 24 of housing 20, ready for use. For example, housing 20 may include structure integrally formed therewith or attached thereto for releasably maintaining needle assembly 40 in such a first position. This may be accomplished in a manner as shown in FIGS. 1-3 through a retainer member 80 co-acting with housing 20. Retainer 80 provides a mechanism for activation to release needle assembly 40 from this first position, thereby permitting the needle assembly 40 to move to a second position in which the intravenous puncture tip 50 is contained within interior chamber 28 of housing 20, as will be discussed in more detail herein.

As depicted in FIGS. 1-3, retainer 80 may be in the form of a flexible band member 82 extending within outer housing 20. Flexible band member 82 is desirably a generally flat band structure, and in one embodiment is integrally formed or otherwise affixed into an integral loop structure to form a continuous band member, as shown in FIG. 5.

Flexible band member 82 is desirably maintained within interior chamber 28 of outer housing 20 in a manner so as to be movable about an internal surface of outer housing 20. For example, an inner housing insert 110 may be provided within the interior chamber 28 of outer housing 20, with flexible band member 82 sandwiched between outer housing 20 and inner housing insert 110. Inner housing insert 110 includes a general profile and shape so as to be readily received within the interior chamber 28 of outer housing 20. Desirably, inner housing insert 110 defines a generally hollow tubular wall 112 which includes a first or forward end 114 and a second or rearward end 116 with tubular wall 112 further defining an interior chamber 118 therein. As with outer housing 20, tubular wall 112 of inner housing insert 110 is desirably of a non-circular cross-sectional profile, such as a square shaped cross-sectional profile as shown. Forward end 114 of inner housing insert 110 includes a forward opening 120 extending therethrough, while rearward end 116 is generally open-ended through rearward opening 122, providing access into interior chamber 118. Such interior chamber 118 accommodates blood sampling tube 16 during a sampling procedure, as is known in the art. Inner housing insert 110 is desirably comprised of moldable parts similar in material as that of outer housing 20.

As noted, inner housing insert 110 provides a mechanism for maintaining flexible band member 82 within interior chamber 28 of outer housing 20. Accordingly, inner housing insert 110 and outer hosing 20 desirably include structure for locking engagement therebetween. For example, inner housing insert 110 may include one or more fingers 124 extending from the outer surface thereof, such as at rearward end 116, for interlocking engagement with one or more corresponding recesses or openings 124 through tubular wall 22 of outer housing 20. Such interlocking engagement provides a mechanism for a snap-fit locking engagement, thereby fixing flexible band member 82 sandwiched between inner housing insert 110 and outer housing 20.

As noted, flexible band member 82 acts as a retainer mechanism to maintain needle assembly 40 in the first position extending from the forward end 24 of housing 20, and also is adapted to activate so as to release the needle assembly 40 from being held in this forward extending position when desired. This is desirably accomplished by providing flexible band member 82 with a series of slots and openings sized to accommodate different portions of needle assembly 40 therethrough. In particular, as shown in detail in FIG. 5, flexible band member 82 is desirably formed of a continuous band member which includes a first portion 83 including a slot 84 which is sufficiently sized to receive non-patient puncture tip 52 therethrough while preventing hub port 66 from passing therethrough. Slot 84 of first portion 83 extends as a continuous slot, opening into a slot opening 86 at second portion 85 of flexible band member 82. Slot opening 86 is sufficiently sized in diameter so as to permit hub port 66 to pass therethrough during retraction, as will be discussed in more detail herein in terms of use of the device. A third portion 87 of flexible band member 82 defines a solid band 88, while a fourth portion 89 defines an opening 90 sized so as to receive tube 16 during a blood sampling procedure. A fifth portion 91 of flexible band 82 defines a solid band 92.

Flexible band member 82 is movable about an internal perimeter within interior chamber 28 of outer housing 20 between outer housing 20 and inner housing insert 110. Such movement may be accomplished by provided a mechanism extending from flexible band member 82 through the tubular wall 22 of outer housing 20. For example, outer housing 20 may include a slot 100 extending axially through the tubular wall 22 along one side thereof between a forward slot end 102 and a rearward slot end 104. Flexible band member 82 may include one or more fingers 94 protruding from the outer surface thereof, which are adapted to extend through slot 100. A separate tab member 96 may be provided for snap-fitting or other type of engagement with fingers 94. Tab member 96 is adapted for sliding engagement along slot 100 between forward slot end 102 and rearward slot end 104, with such movement of tab member 96 effecting corresponding movement of flexible band member 82, as will be discussed in more detail herein.

Blood collection device 10 is assembled by wrapping or otherwise extending flexible band member 82 about tubular wall 112 of inner housing insert 110, such that first portion 83 of flexible band member 82 is adjacent forward end 114 of inner housing insert 110 with slot 84 in alignment with forward opening 120, and with fourth portion 89 of flexible band member 82 adjacent rearward end 116 such that opening 90 of flexible band member 82 is in alignment with rearward opening 120 of inner housing insert 110. Hub port 66 is inserted within outer housing 20 such that skirt 72 extends into forward opening 30 and into depending skirt 36, with nubs 76 on the exterior surface of skirt 72 of hub port 66 in alignment between corresponding nubs 38 within forward opening 30 at depending skirt 36 of outer housing 20. The forward end 114 of inner housing insert 110, with flexible band member 82 extending thereabout, may then be inserted through rearward opening 32 and into the interior chamber 28 of outer housing 20, with fingers 124 of inner housing insert 110 snap-fitting within openings 126 of outer housing 20. In this manner, hub port 66 is situated within outer housing 20 and wedged between first portion 83 of flexible band member 82 and the forward end 24 of outer housing 20, with the internal opening 68 of hub port 66 in alignment with slot 84 of flexible band member 82 and in alignment with forward opening 120 of inner housing insert 110. The outer diameter and/or profile of flange 74 of hub port 66 prevents hub port 66 from extending or passing all the way through forward opening 30 of outer housing 20 in a forward direction, and prevents hub port 66 from extending or passing all the way through slot 84 at first portion 83 of flexible band member 82 in a rearward direction. Further, fingers 94 of flexible band member 82 extend through slot 100 at a side of tubular wall 22 of outer housing 20. Tab 96 is fitted with fingers 94 in a fixed relationship, at a forward slot end 102 of slot 100.

After assembly in this manner, needle assembly 40 can be assembly with holder 12. For example, the non-patient puncture tip 52 with elastomeric sleeve 62 thereover is passed into forward opening 30 at forward end 24 of outer housing 20, through slot 84 at first portion 83 of flexible band member 82, and into the interior chamber 118 within inner housing insert 110. External threads 60 on the outer surface of hub 54 are threadably engaged with internal threads 70 within internal opening 68 of hub port 66. During such threading engagement, rotation of hub port 66 is prevented through the interfitting relationship of nubs 76 of hub port 66 and nubs 38 within the forward opening 30 at depending skirt 36 of outer housing 20. Blood collection device 10 may then be packaged in a conventional sterile package, such as a blister package (not shown) or other packaging methods known to provide such a device as a sterile, ready to use assembly.

Prior to use, the blood collection device 10 is removed from its package and, if necessary, any protective cover (not shown) extending about the intravenous puncture tip 50 of needle cannula 42 is removed. Blood collection device 10 is thereafter ready for use in a blood collection procedure.

To use the blood collection device 10, venipuncture is conducted in a known manner, whereby intravenous puncture tip 50 at forward end 44 of needle cannula 42 is inserted into a target blood vessel of a patient in order to conduct a blood collection procedure or other procedure as desired. An evacuated tube 16 having a piercable closure 18 is then inserted into rearward opening 32 of outer housing 20, through opening 90 of flexible band member 82 and through rearward opening 122 of inner housing insert 110 and into interior chamber 118, such that the piercable closure 18 of the evacuated tube 16 contacts sleeve 62 extending about non-patient puncture tip 52. When pressure is exerted on the evacuated tube 16 in the axial direction toward the forward end of the device, the piercable closure 18 contacting sleeve 62 causes sleeve 62 to displace, thereby causing non-patient puncture tip 52 to puncture sleeve 66 and, in turn, the piercable closure 18 of the evacuated tube 16. At such time, the interior of the evacuated tube 16 and lumen 48 of needle cannula 42 are in fluid communication. Since the interior of the evacuated tube 16 is at a negative pressure, blood is drawn from the vein of the patient, through lumen 48 of needle cannula 42 and into the evacuated tube 16. Multiple samples can be drawn into a number of successive evacuated tubes in this manner.

Figure 7A:
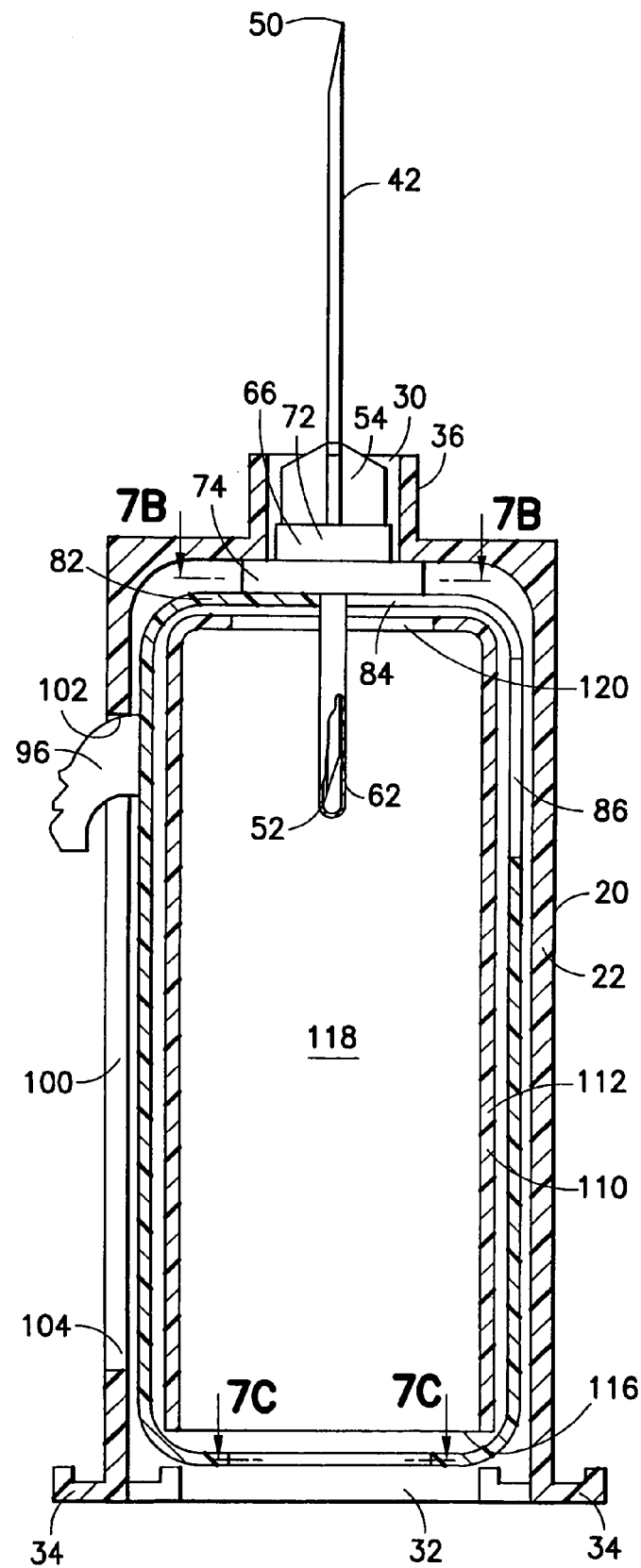
FIG. 7A is a partial sectional view of the safety blood collection device of FIG. 1 shown in an upright position in the first position with the needle cannula extending from the forward end of the holder housing.

When all desired samples have been drawn, evacuated tube 16 is withdrawn from interior chamber 118 and release of the needle assembly 40 from the holder 12 is accomplished. In particular, at this point, blood collection device 10 is at an initial position, or Stage 0, as shown in FIGS. 7A-7C, with needle assembly 40 in a first position with forward end 56 of needle cannula 42 extending from forward end 24 of outer housing 20. As shown in FIG. 7B, needle assembly 40 is maintained in this first position through port flange 74 of hub port 66 including an outer diameter larger than the slot 84 of first portion 83 of flexible band member 82, thereby being held in place. As shown in FIG. 7C, opening 90 of fourth portion 89 of flexible band member 82 is in alignment with rearward opening 122 of inner housing insert 110 and rearward opening 30 of outer housing 20 at this initial, stage 0 position. Retainer 80 provided through flexible band member 82 is also in a first position, with tab 92 at the forward slot end 102 of outer housing 20.

Figure 8A:
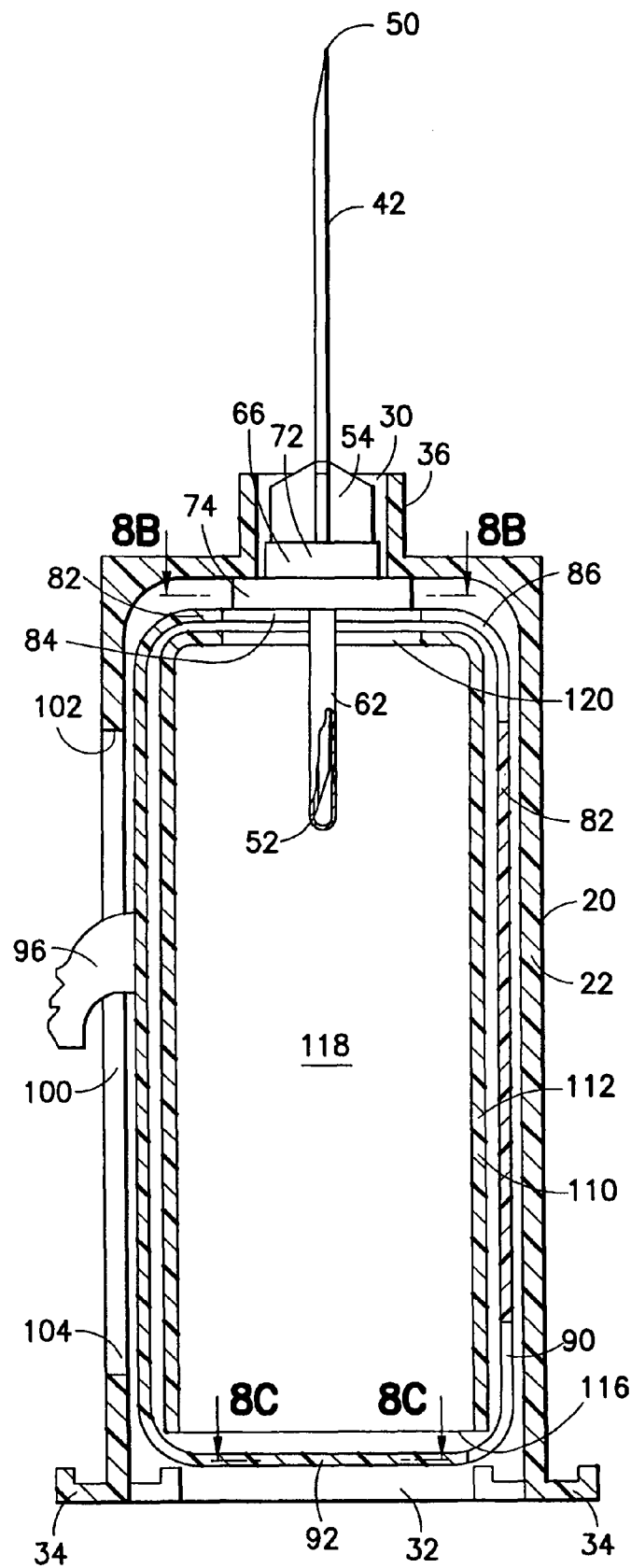
FIGS. 8A and 9A are partial sectional views of the safety blood collection device of FIG. 1 shown in an upright position during movement of the retainer from the first position to the second position.

Release of the needle assembly 40 is accomplished by activation of retainer 80, that is by movement of flexible band member 82 from the first position shown in FIG. 7A toward a second position, shown through FIGS. 8A-9C and 9A-9C, desirably while blood collection device 10 is in an upright position, although it is also contemplated that activation can be accomplished first followed by later positioning of blood collection device 10 into an upright position. A user contacts tab 96 with a finger and moves tab 96 from the initial position adjacent forward slot end 102 toward rearward slot end 104, shown in FIG. 8A, representing blood collection device 10a in a Stage 1 position. During such movement, flexible band member 82 travels between and interior surface of outer housing 20 and about an outer surface of inner housing insert 110 in a perimetrical loop. As shown in FIG. 8B, during such initial movement, first portion 83 of flexible band member 82 remains adjacent forward opening 30 of outer housing 20, such that the non-patient puncture tip 52 at rearward end 46 of needle cannula 42 extends through slot 84 and such that port flange 74 remains in interference engagement with the surface of flexible band member 82 surrounding slot 84 at the first portion 83, preventing rearward movement of needle assembly 40. As shown in FIG. 8C, during this initial movement fourth portion 89 of flexible band member 82 moves away from rearward openings 32, 122, and fifth portion 91 of flexible band member 82 extends across rearward openings 32, 122, such that solid band 92 closes off the rearward openings 32, 122, preventing access to the interior chamber 118 therein.

Figure 9A:
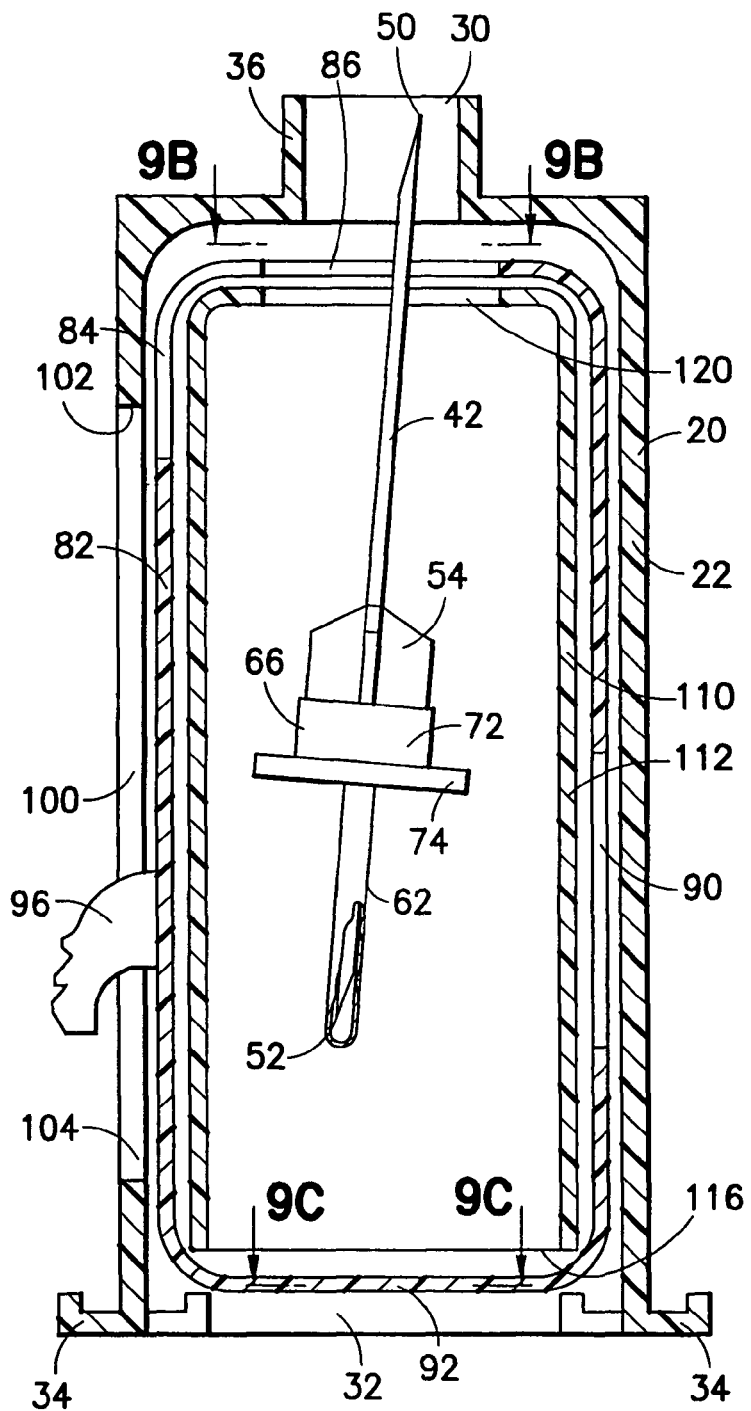
Figure 9B:
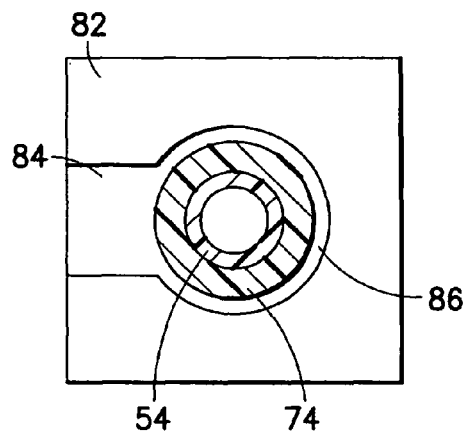
Figure 9C:
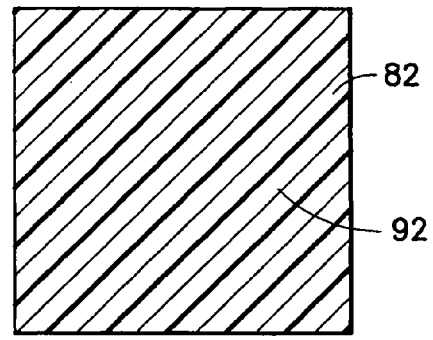

Continued movement of tab 96 toward the rearward slot end 104 results in continued movement of flexible band member 82 between outer housing 20 and inner housing insert 110, as shown in FIG. 9A with blood collection device at a Stage 2 position. During such continued movement, second portion 85 of flexible band member 82 is moved such that slot opening 86, which is contiguous with slot 84, is moved into alignment with forward opening 30 at the forward end 24 of outer housing 20. Slot opening 86 includes a diameter which is at least slightly larger than the outer diameter of port flange 74 of hub port 66. Accordingly, as shown in FIG. 9B, such alignment causes hub port 66 to align with slot opening 86. With blood collection device 10 in an upright position, the force of gravity causes hub port 66, and needle assembly 40 attached hereto through hub 54, to move or drop through slot opening 86 and into interior chamber 118 within inner housing insert 110 of holder 12. Since the overall length of needle assembly 40, and in particular needle cannula 42 is shorter than holder 12, non-patient puncture tip 52 is maintained within interior chamber 118 of holder 12 even after intravenous puncture tip 50 falls beyond forward openings 30, 120. As shown in FIG. 9C, fifth portion 91 of flexible band member 82 extends across rearward openings 32, 122, at this Stage 2 position with solid band 92 closing off the rearward openings 32, 122 and preventing needle assembly 40 from passing through the rearward openings 32, 122.

Figure 10B:
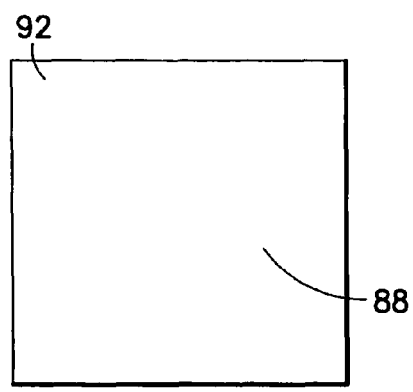
FIG. 10B is a top down view taken alone line 10B-10B of FIG. 10A.
Figure 10C:
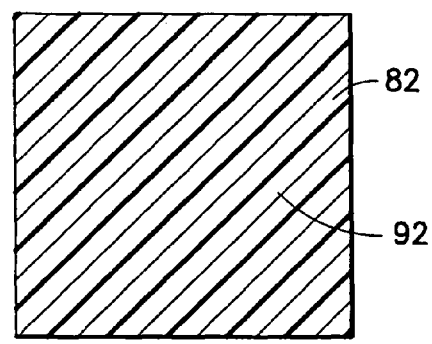
FIG. 10C is a bottom up view taken alone line 10C-10C of FIG. 10A.
Figure 10A:
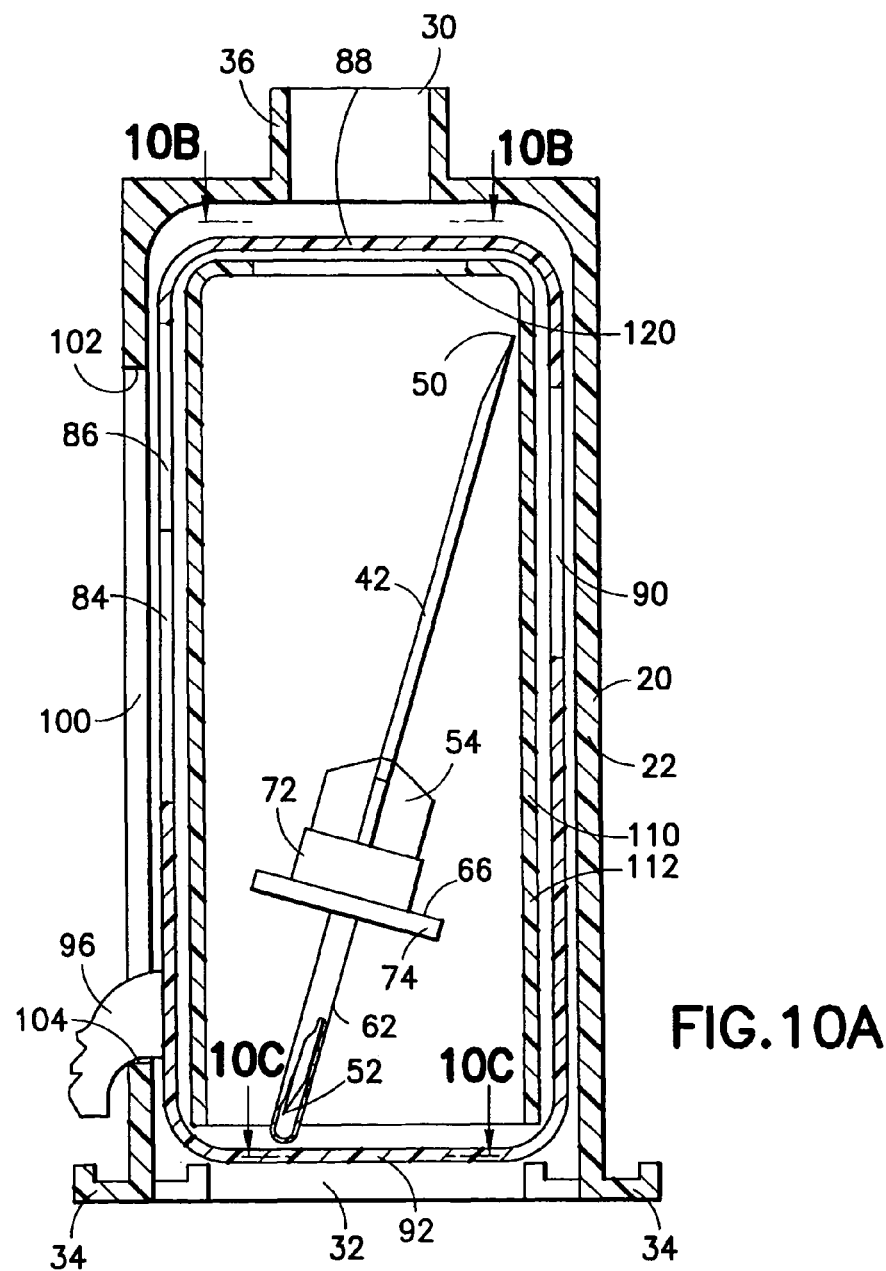
FIG. 10A is a partial sectional view of the safety blood collection device of FIG. 1 shown in an upright position after the needle cannula has been dropped to the second position contained within the holder housing.

Further movement of tab 96 to the rearward slot end 104 results in continued movement of flexible band member 82 between outer housing 20 and inner housing insert 110, as shown in FIG. 10A with blood collection device at a Stage 3 or final position. In this position, third portion 87 of flexible band member 82 is moved to a position such that sold band 88 extending across forward openings 120, 30 of inner housing insert 110 and outer housing 20, respectively, thereby closing off access to the interior chamber 118 through such openings, as shown in FIG. 10B. Fifth portion 91 of flexible band member 82 continues to extend across rearward openings 32, 122, at this Stage 3 position with solid band 92 closing off the rearward openings 32, 122, as shown in FIG. 9C. Further, flexible band member 82 may be locked into this Stage 3 position to prevent any reverse movement. For example, tab 96 of flexible band member 82 may be locked into detents 106 extending into slot 100, providing for an interference engagement therewith. Accordingly, flexible band member 82 is locked in position from further movement with respect to holder 12, and needle assembly 40 is safely contained therein, with intravenous puncture tip 50 and non-patient puncture tip 52 rendered inaccessible. Blood collection device 10 can then be appropriately discarded.

FIGS. 11-20 depict further embodiments of the present invention, and include many components which are substantially identical to the components of FIGS. 1-10. Accordingly, similar components performing similar functions will be numbered identically to those components of FIGS. 1-10, except that a suffix "a" will be used to identify those similar components in FIGS. 11-15, a suffix "b" will be used to identify those similar components in FIGS. 16-18, and a suffix "c" will be used to identify those similar components in FIGS. 19-20.

FIGS. 11-15 depict an alternate embodiment of the invention with an alternate retainer structure for effecting activation to release the needle assembly and permit the force of gravity to drop the needle assembly into a safely contained position. In particular, in the embodiment of FIGS. 11-15, the retainer is in the form of a ring structure 130 which extends within the interior chamber 28a of outer housing 20a which defines holder 12a. More particularly, blood collection device 10a includes holder 12a in the form of outer housing 20a including tubular wall 22a extending between forward end 24a and rearward end 26a to define interior chamber 28a therebetween. Forward opening 30a extends through forward end 24a, and rearward end 26a is generally open-ended defining rearward opening 32a. Flange 34a may circumscribe at least a portion of the rearward end 26a, while depending skirt 36a may extend about forward opening 30a at forward end 24a.

Blood collection device 10a also includes needle assembly 40a adapted for assembly with holder 12a. Needle assembly 40a includes a needle cannula 42a extending between a forward end 44a having an intravenous puncture tip 50a and a rearward end 46a having a non-patient puncture tip 52a, and with a lumen 48a extending therethrough. Needle cannula 42a is assembled with a needle hub 54a, including a forward end 56a and an opposed rearward end 58a. The rearward end 58a of hub 54a includes an external portion or structure for mating with a portion of needle holder 12a, such as external threads 60a. Needle assembly 40a may further include an elastomeric sleeve 62a extending about non-patient puncture tip 52a of needle cannula 42a.

In the embodiment described in FIGS. 11-15, the retainer takes the form of a rotating ring structure 130, as opposed to the flexible band member (82) described with reference to FIGS. 1-10. As such, the blood collection device 10a of FIGS. 11-15 does not include any corresponding inner housing insert 110 to maintain such a flexible band member in place within the outer housing 20. Blood collection device 10a, however, does include an internal carrier structure 140 for affixing needle assembly 40a to holder 12a and for maintaining and carrying needle assembly 40a during use, as will be discussed.

Figure 12:
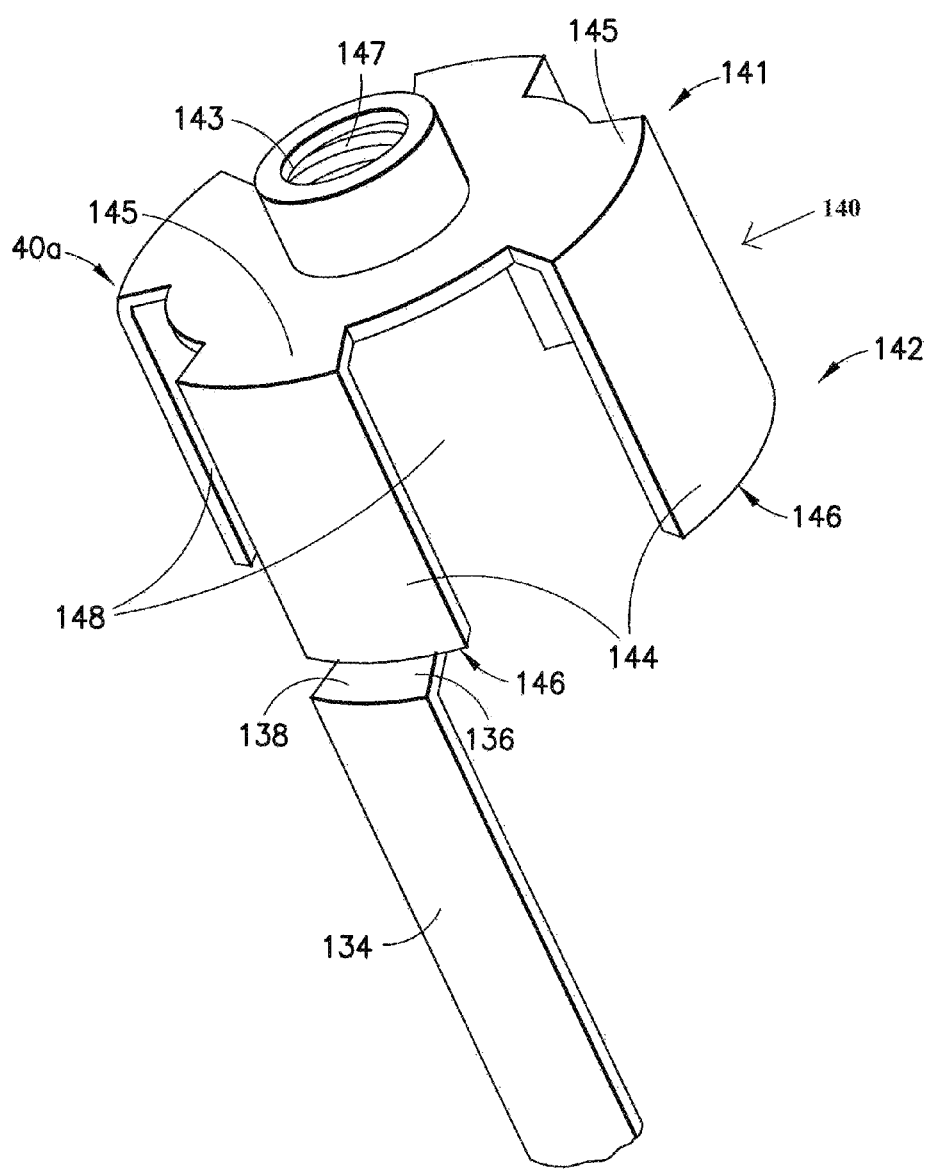
FIG. 12 is a perspective view of a rotatable ring structure for use in the embodiment of FIG. 11.

In particular, carrier 140 is positioned within interior chamber 28a of outer housing 20a. As shown in FIG. 12, carrier 140 includes a general framework including a forward end 141 and a rearward end 142. Forward end 141 includes a hub port 143 adapted for interconnection with needle hub 54a of needle assembly 40a at forward end 24a. Such interconnection may be provided, for example, through a threaded or a snap-fit attachment, or through permanent bonding. In one embodiment, hub port 143 may include structure on an internal surface thereof for engagement with an external surface of needle hub 54a, such as internal threads 147 for threaded engagement with corresponding external threads on the outer surface of needle hub 54a, as with the embodiment shown in FIGS. 1-10. As such, a standard conventional double-ended needle can be used as needle assembly 40a in conjunction with carrier 140. Alternately, needle hub 54a and/or needle cannula 52a may be integrally formed with carrier 140.

As shown in FIG. 12, carrier 140 further includes at least one, and preferably a plurality of legs 144 extending toward the rearward end 142 of carrier 140 between forward leg surfaces 145 and rearward leg surfaces 146. Extending between each of these legs 144 are gaps 148. The external diameter of carrier 140 defined by the outer surfaces of legs 144 is slightly less than the internal diameter of tubular wall 22a of outer housing 20a, such that carrier 140 is adapted for sliding movement within interior chamber 28a. Moreover, the length of legs 144 are preferably equal to or slightly longer than the length of rearward end 46a of needle cannula 42a extending between non-patient puncture tip 52a and the rearward end 58a of needle hub 54a. In this manner, non-patient puncture tip 52a does not extend beyond legs 144 when needle assembly 40a is assembled with carrier 140.

Carrier 140 is adapted for movement within interior opening 28a of outer housing 20a of holder 12a from a first position in which intravenous puncture tip 50a extends from forward end 24a of outer housing 20a through forward opening 30a, to a second position in which intravenous puncture tip 50a and non-patient puncture tip 52a are contained entirely in the interior chamber 28a within outer housing 20a. This is accomplished by providing a retainer in the form of ring structure 130.

Figure 11:
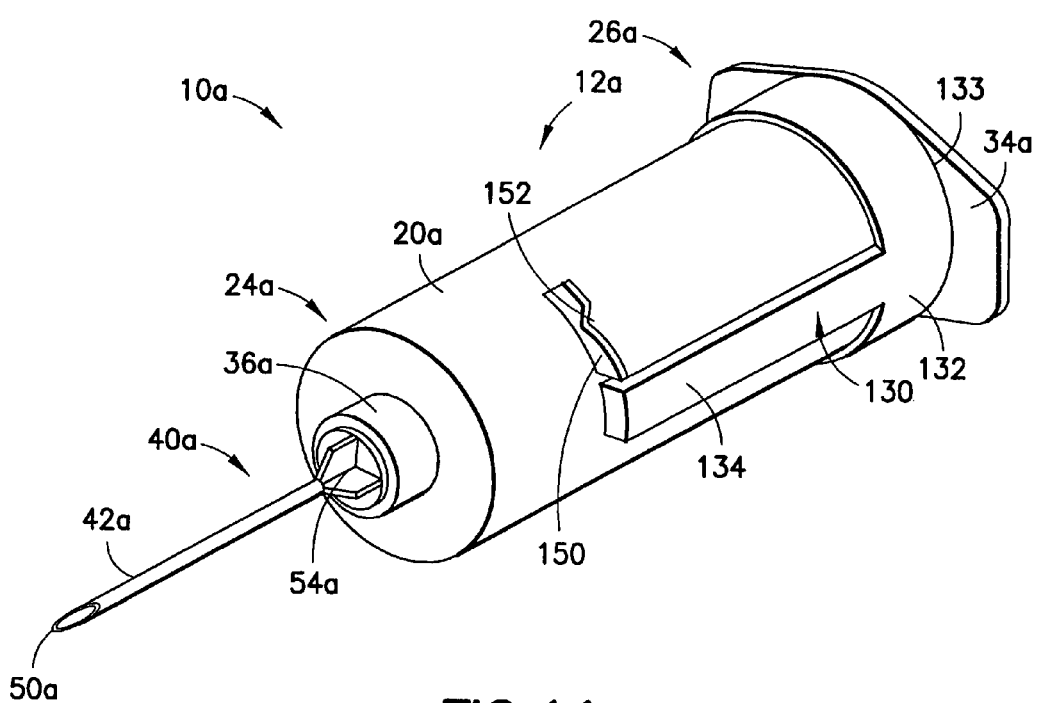
FIG. 11 is a perspective view of a safety blood collection device in accordance with an alternate embodiment of the invention.

More particularly, ring structure 130 includes an annular ring 132 extending about an external surface of tubular wall 22a defining outer housing 20a adjacent rearward end 26a thereof. Ring structure 130 includes an internal diameter which is desirably slightly greater than the external diameter of tubular wall 22a defining outer housing 20a. As shown in FIG. 11, the rearward edge 133 of annular ring 132 desirably rests against a top surface of flange 34a of outer housing 20a. Ring structure further includes at least one, and preferably a pair of support arms 134 extending from annular ring 132 toward the forward end 24a of outer housing 20a, desirably along an external surface of outer housing 20a.

Figure 13:
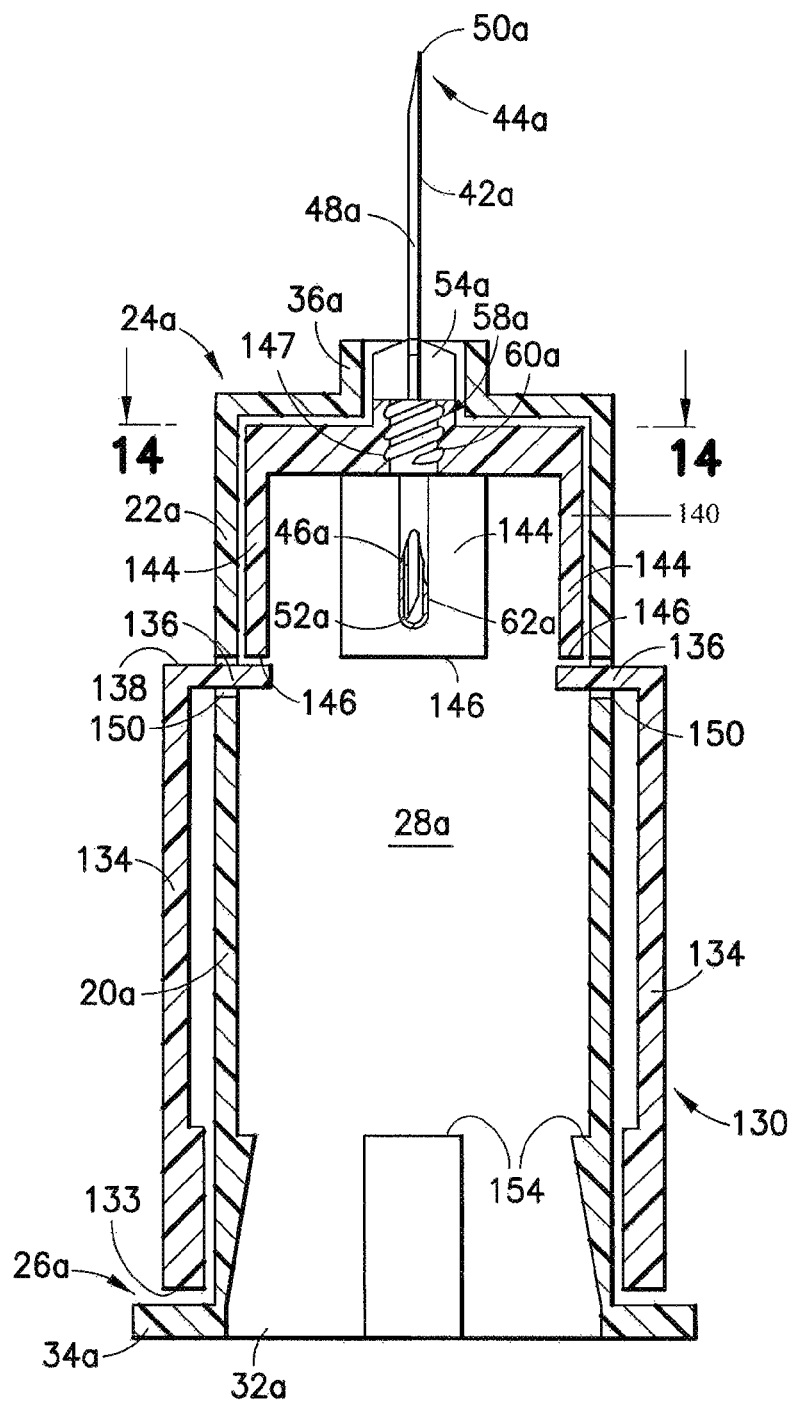
FIG. 13 is a cross-sectional view of the safety blood collection device of the embodiment of FIG. 11 shown in an upright position in the first position with the needle cannula extending from the forward end of the holder housing.

Support arms 134 include fingers 136 at the forward end thereof. Fingers 136 extend through tubular wall 22a of outer housing 20a and into interior chamber 28a. In particular, outer housing 20a includes housing slots 150 extending through tubular wall 22a in a direction perpendicular to axis A, about the perimeter of tubular wall 22a. Fingers 136 extend from support arms 134 at the outside outer housing 20a and through tubular wall 22a at housing slots 150. In this manner, fingers 136 of ring structure 130 provide a point of contact for interference engagement with carrier 140. In particular, with fingers 136 extending through housing slots 150, rearward leg surfaces 146 of carrier 140 rest upon upper surfaces 138 of fingers 136, providing for an interfering or abutting engagement therebetween, as shown in FIG. 12. Such engagement maintains needle assembly 40a in a first position as shown in FIG. 13, with carrier 140 provided within interior chamber 28a of outer housing 20a, with intravenous puncture tip 50a extending from forward end 24a of outer housing 20a, and with non-patient puncture tip 52a contained within interior chamber 28a of outer housing 20a.

In such a first position, blood collection device 10a is ready for sampling during a blood collection procedure, as discussed hereinabove.

Figure 14:
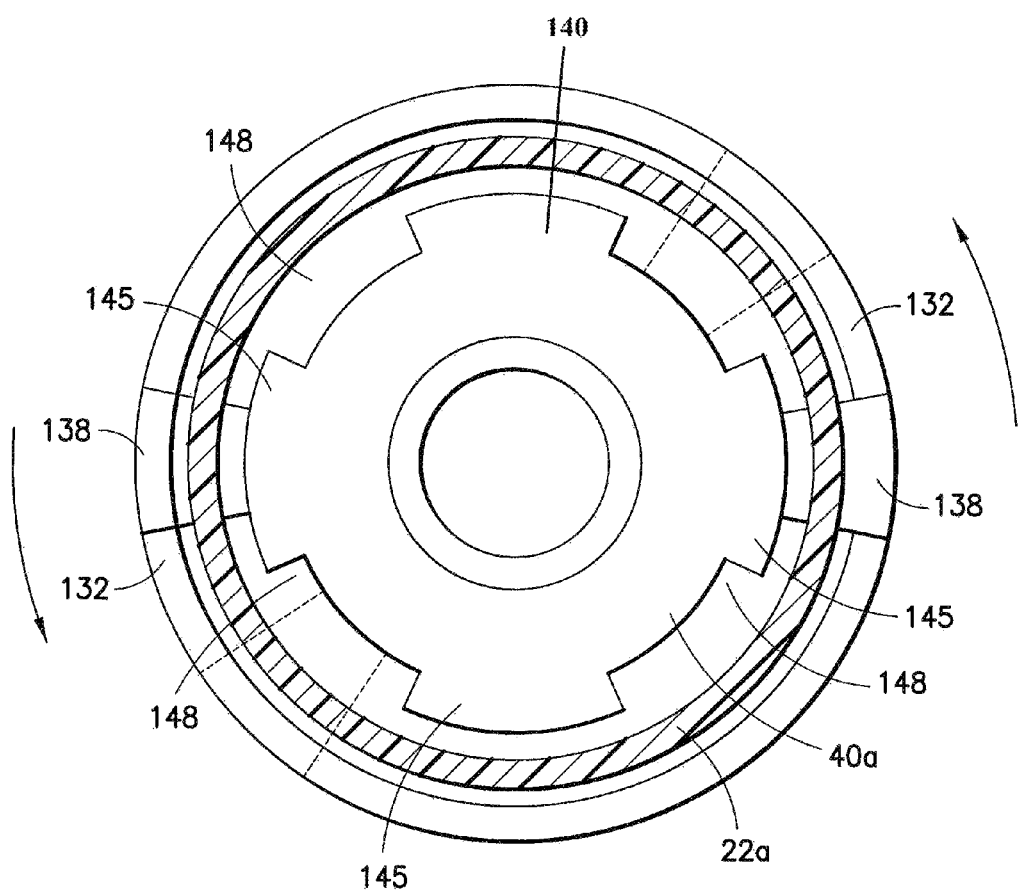
FIG. 14 is a top down view taken along line 14-14 of FIG. 13.
Figure 15:
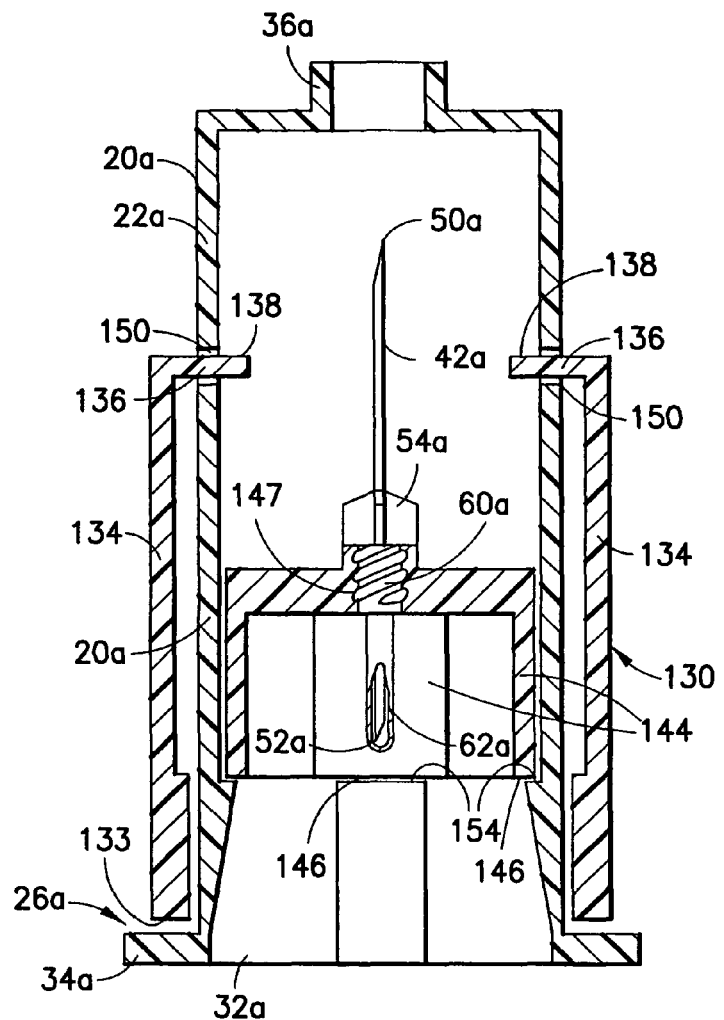
FIG. 15 is a cross-sectional view of the safety blood collection device of the embodiment of FIG. 11 shown in an upright position after the needle cannula has been dropped to the second position contained within the holder housing.

After use of blood collection device 10a, activation of the retainer feature provides for safe containment of the needle assembly 40a. In particular, ring structure 130 is rotatable with respect to outer housing 20a, which causes activation of the retainer feature provided through ring structure 130. As shown in FIG. 14, to effect actuation of blood collection device 10a, ring structure 130 is rotated such that fingers 136 slide along and through housing slots 150 from a first position in which fingers 136 abut against rearward leg surfaces 146 of carrier 140, to a second position in which fingers 136 align within gaps 148 between legs 144 (shown at the dotted lines of FIG. 14). At such point, the interfering or abutting engagement between upper surfaces 138 of fingers 136 and rearward leg surfaces 146 of carrier 140 is released. With blood collection device 10a in an upright position, the force of gravity causes carrier 140, and needle assembly 40a attached thereto, to move or drop into interior chamber 28a within outer housing 20a of holder 12a to a second position as shown in FIG. 15. Since the overall length of needle assembly 40a, and in particular needle cannula 42a, is shorter than holder 12a, non-patient puncture tip 52a is maintained within interior chamber 28a of holder 12a even after intravenous puncture tip 50a falls beyond forward opening 30a, as shown in FIG. 15.

Desirably, alignment of fingers 136 with gaps 148 is accomplished at a first rotative position of ring structure 130 before fingers 136 travel the full distance of housing slots 150. In this manner, continued rotation of ring structure 130 permits fingers 136 to travel the full distance of housing slots 150, such that fingers 136 extend into interior chamber 28a at a position aligning them with the forward surfaces 145 of carrier 140. In this manner, a reverse travel of carrier 140 through holder 12a and re-exposure of intravenous puncture tip 50a is prevented, even if holder 12a is turned over in an up-ended position. Blood collection device 10a may further include a mechanism to prevent reverse rotation of ring structure 130 to further prevent re-exposure of intravenous puncture tip 50a. For example, housing slots 150 may also include a detent 152 for interference engagement with fingers 136 once they pass beyond detent 152, thereby locking ring structure 130 in the second, rotated position.

Moreover, carrier 140 is prevented from extending entirely through interior chamber 28a and falling out of rearward opening 32a. This may be accomplished through one or more internal abutments 154 providing for abutting engagement with the rearward leg surfaces 146 of carrier 140 when carrier 140 is dropped within interior chamber 28a. Since the length of legs 144 are equal to or slightly longer than the length of rearward end 46a of needle cannula 42a, non-patient puncture tip 52a does not extend beyond legs 144. Moreover, with internal abutments 154 spaced from rearward opening 32a, non-patient puncture tip 52a is maintained within interior chamber 28a a sufficient distance to prevent access thereto through rearward opening 32a. Furthermore, the overall length of needle assembly 40a including carrier 140 attached or affixed thereto is less than the length of the body portion of outer housing 20a extending between the internal abutments 154 and the forward end wall defining forward end 24a. As such, needle assembly 40a is safely contained entirely within holder 12a.

Figure 16:
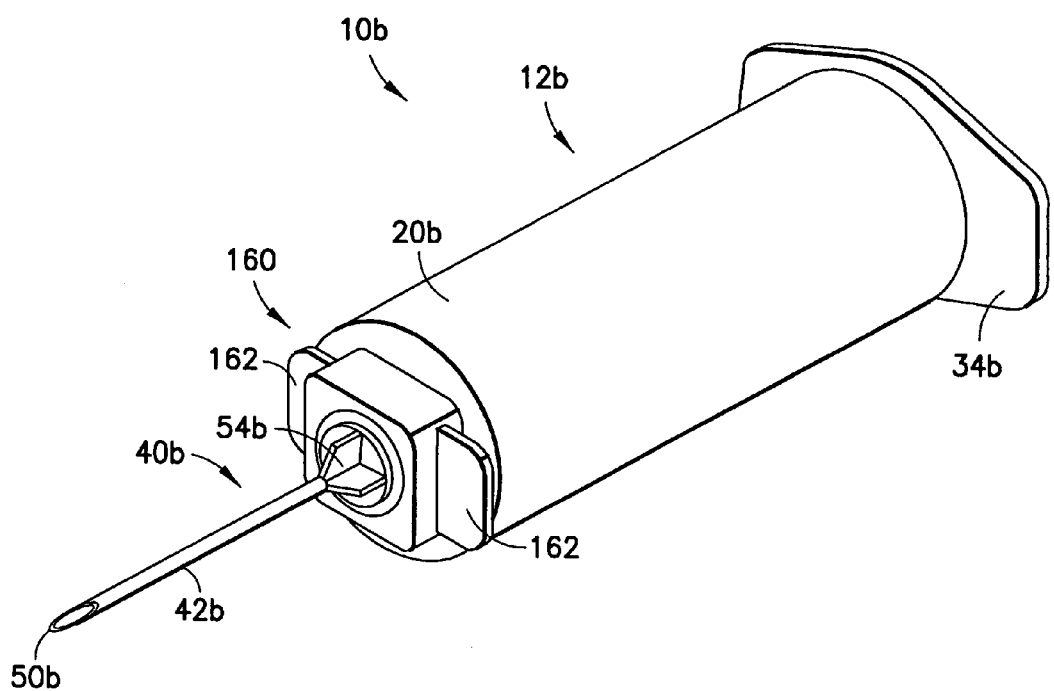
FIG. 16 is a perspective view of a safety blood collection device in accordance with a further alternate embodiment of the invention.
Figure 17:
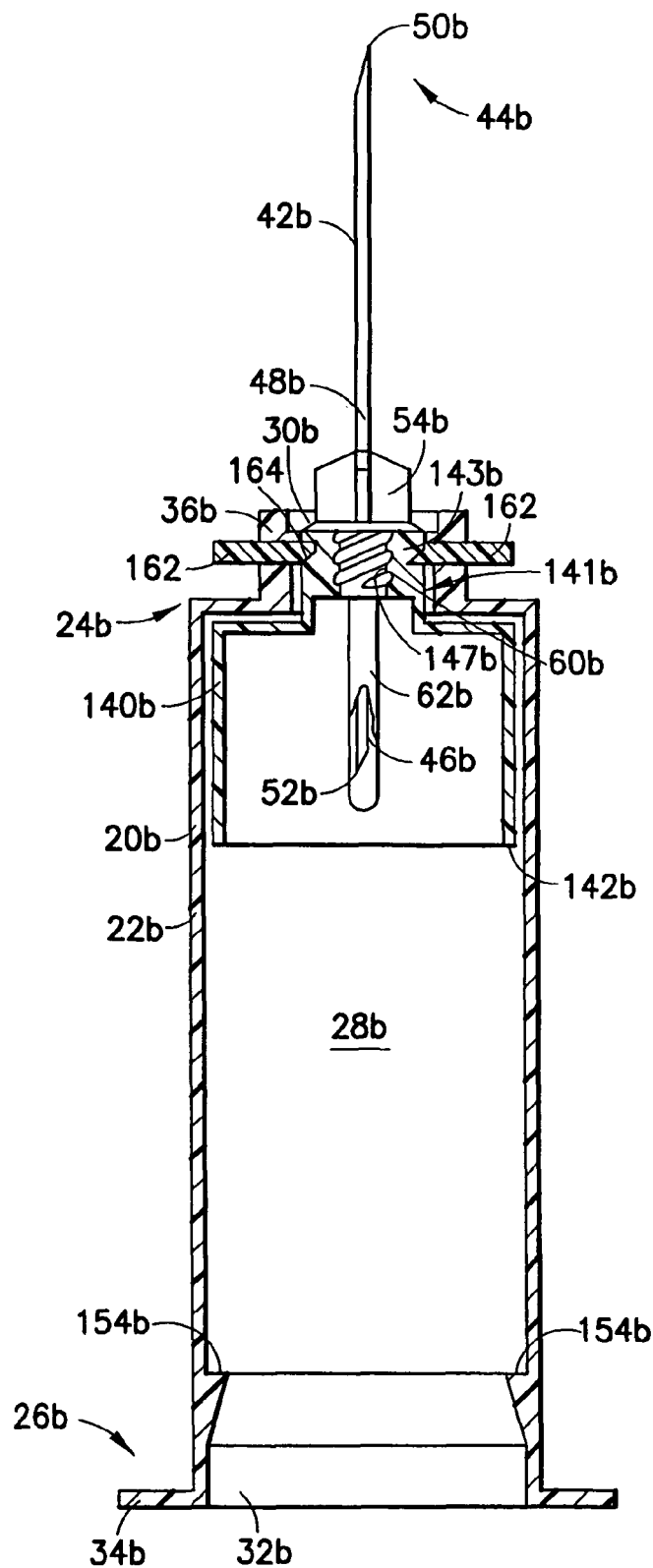
FIG. 17 is a cross-sectional view of the safety blood collection device of the embodiment of FIG. 16 shown in an upright position in the first position with the needle cannula extending from the forward end of the holder housing.
Figure 18:
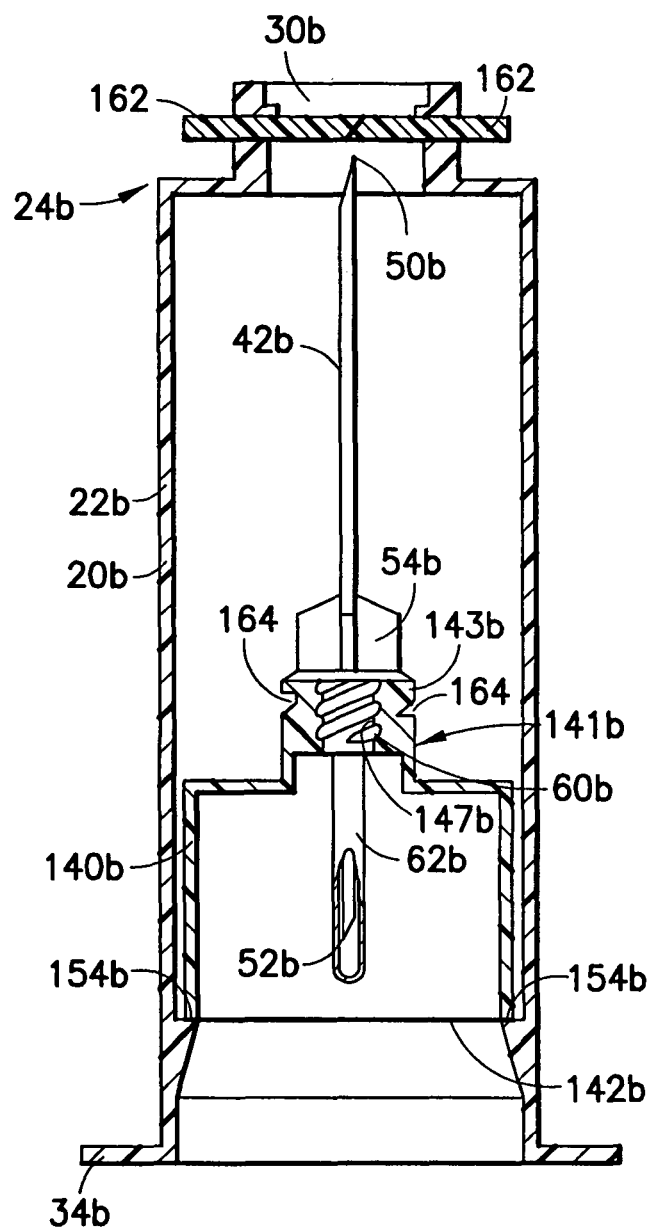
FIG. 18 is a cross-sectional view of the safety blood collection device of the embodiment of FIG. 16 shown in an upright position after the needle cannula has been dropped to the second position contained within the holder housing.

A further embodiment is described with reference to FIGS. 16-18. In particular, in the embodiment depicted in FIGS. 16-18, blood collection device 10b includes a holder 12b defined by an outer housing 20b including tubular wall 22b extending between forward end 24b and rearward end 26b to define interior chamber 28b therebetween. Forward opening 30b extends through forward end 24b, and rearward end 26b is generally open-ended defining rearward opening 32b. Flange 34b may circumscribe at least a portion of the rearward end 26b, while depending skirt 36b may extend about forward opening 30b at forward end 24b.

Blood collection device 10b also includes needle assembly 40b adapted for assembly with holder 12b. Needle assembly 40b includes a needle cannula 42b extending between a forward end 44b having an intravenous puncture tip 50b and a rearward end 46b having a non-patient puncture tip 52b, and with a lumen 48b extending therethrough. Needle cannula 42b is assembled with a needle hub 54b, including a forward end 56b and an opposed rearward end 58b. The rearward end 58b of hub 54b includes an external portion or structure for mating with a portion of needle holder 12b, such as external threads 60b. Needle assembly 40b may further include an elastomeric sleeve 62b extending about non-patient puncture tip 52b of needle cannula 42b.

As with the embodiment of FIGS. 11-15, needle assembly 40b is affixed to holder 12b through an internal carrier structure 140b for maintaining and carrying needle assembly 40b during use. In particular, carrier 140b is positioned within interior chamber 28b of outer housing 20b. As shown in FIG. 17, carrier 140b includes a forward end 141b and a rearward end 142b, with forward end 141b including a hub port 143b adapted for interconnection with needle hub 54b of needle assembly 40b, such as through internal threads 147b for threaded engagement with corresponding external threads 60b on the outer surface of needle hub 54b. Alternately, needle hub 54b and/or needle cannula 52b may be integrally formed with carrier 140b.

Carrier 140b includes a body structure extending toward the rearward end 142b of carrier 140b between forward end 141b and rearward end 142b. The external diameter of carrier 140b is slightly less than the internal diameter of tubular wall 22b of outer housing 20b, such that carrier 140b is adapted for sliding movement within interior chamber 28b. Moreover, the length of carrier 140b is preferably equal to or slightly longer than the length of rearward end 46b of needle cannula 42b extending between non-patient puncture tip 52b and the rearward end 58b of needle hub 54b, such that non-patient puncture tip 52b does not extend beyond carrier 140b.

Carrier 140b is adapted for movement within interior opening 28b of outer housing 20b of holder 12b from a first position in which intravenous puncture tip 50b extends from forward end 24b of outer housing 20b through forward opening 30b to a second position in which intravenous puncture tip 50b and non-patient puncture tip 52b are contained entirely within the interior chamber 28b within outer housing 20b. This is accomplished by providing a retainer in the form of clamping mechanism 160.

Clamping mechanism 160 generally includes a pair of claws 162 adapted to grasp a portion of carrier 140b, thereby maintaining the needle assembly 40b in the first position. In particular, carrier 140b may include grooves 164 for interference engagement with a corresponding surface of claws 162. To effect release of carrier 140b, claws 162 are activated, which may involve pressing the claws 162 or tilting of claws 162 out of engagement with grooves 164. Such movement releases the interference engagement, thereby permitting carrier 140b with needle assembly 40b attached thereto to drop within interior chamber 28b of housing 20b based on the force of gravity. The rearward end 142b of carrier 140b abuts against internal abutments 154b spaced from rearward opening 32b, such that non-patient puncture tip 52b is maintained within interior chamber 28b a sufficient distance to prevent access thereto through rearward opening 32b. Furthermore, the overall length of needle assembly 40b including carrier 140b attached or affixed thereto is less than the length of the body portion of outer housing 20b extending between the internal abutments 154b and the forward end wall defining forward end 24b. Claws 162 may further be extendable to cover and close off forward opening 30b at forward end 24b of housing 20b, thereby safely containing needle assembly 40b therein.

While the clamping mechanism is described herein in terms of a specific embodiment, it is contemplated that it may comprise any mechanism known in the art to hold a conventional double-ended needle assembly to a needle holder for quick release from the holder into a sharps container, with such a mechanism modified for the present invention so as to release the needle assembly into and within the needle holder, as opposed to a conventional technique of releasing it from the needle holder. For example, the clamping mechanism may be modified from that disclosed in U.S. Pat. No. 6,306,118 to Crawford et al., the entire disclosure of which is incorporated herein by reference thereto, with such modifications enabling quick and simple release of the needle assembly from a first position with the needle extending from the forward end of the holder for use, to a second position in which the needle drops into the modified holder when in an upright position based on the force of gravity, to be contained therein. Such a modification envisions a departure from the intent of such quick-release assemblies, in that disposal of the entire device with the needle safely contained within the holder is desired, as opposed to re-use of the holder with a new needle assembly as is the conventional intent of such a quick-release holder.

Figure 19:
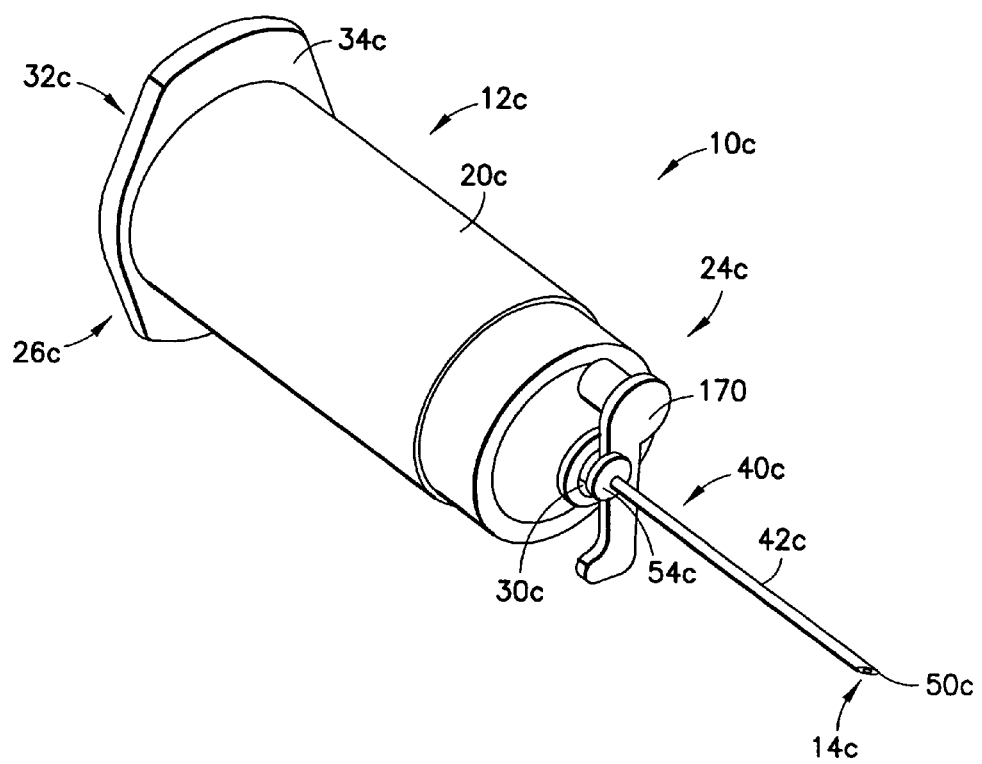
FIG. 19 is a perspective view of a safety blood collection device in accordance with a further alternate embodiment of the invention.
Figure 20:
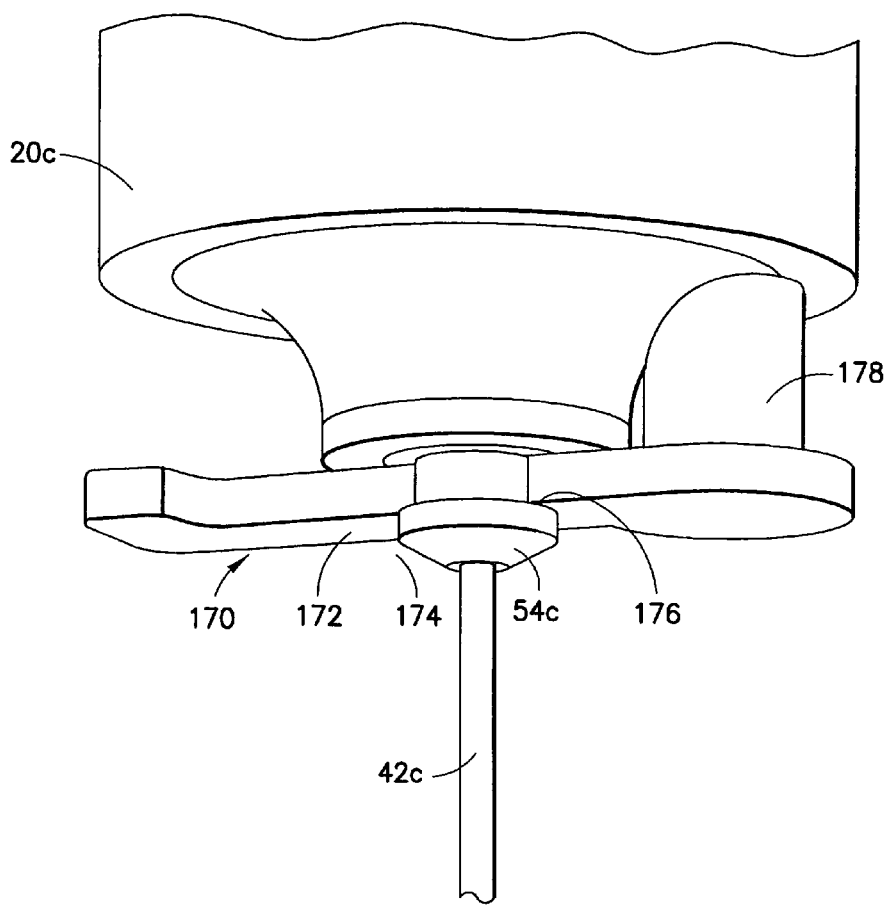
FIG. 20 is an enlarged perspective view of the forward end of the blood collection device of FIG. 19.

FIGS. 19-20 depict a further embodiment in the form of blood collection device 10c, which includes a holder 12c defined by an outer housing 20c extending between forward end 24c and rearward end 26c to define an interior chamber therein. Forward opening 30c extends through forward end 24c, and rearward end 26c is generally open-ended defining rearward opening 32c, circumscribed by flange 34c. Blood collection device 10c also includes needle assembly 40c similar to those described above, adapted for assembly with holder 12c. Needle assembly 40c includes a needle cannula 42c extending between a forward end 44c having an intravenous puncture tip 50c, and further includes a rearward end having a non-patient puncture tip and a lumen extending therethrough, as described in connection with the above embodiments. Needle cannula 42c is assembled with needle hub 54c, which includes an external portion or structure for mating with a portion of needle holder 12c. Desirably, needle assembly 40c is mated with holder 12c through an internal carrier structure such as those described above in connection with FIGS. 11-18, for maintaining and carrying needle assembly 40c during use. In particular, needle hub 54c of needle assembly 40c may be assembled or integrally formed with a carrier, such as carrier 140b shown in FIGS. 16-18 positioned within the interior chamber of outer housing 20c.

In the embodiment of FIGS. 19-20, holder 12c includes arm 170 at forward end 24c thereof. Arm 170 may include a lever structure 172 which extends at least partially across a portion of the forward end 24c of holder 12c. Lever 172 further includes a surface 174 which engages a shoulder 176 of hub 54c in an interference engagement. In this manner, arm 170 maintains hub 54c, and therefore needle assembly 40c, in the first position with intravenous puncture tip 50c extending from the forward end 24c of housing 12c.

Arm 170 may be integrally formed or otherwise attached to outer housing 20c of holder 12c. For example, arm 170 may be integrally formed with outer housing 20c through a living hinge 178. Living hinge 178 provides arm 170 with the ability to move with respect to outer housing 20c between a first position in which surface 174 of arm 170 is in interfering engagement with shoulder 176 of hub 54c to maintain intravenous puncture tip 50c extending from the forward end 24c of housing 12c, and a second position (not shown) in which surface 174 of arm 170 is moved out of engagement with shoulder 176. Such movement releases the interference engagement, thereby permitting hub 54c with needle assembly 40c attached thereto (as well as any carrier element extending within the housing) to drop within the interior chamber of housing 20c based on the force of gravity. Needle assembly 40c is maintained within housing 20c, such as through a carrier element limiting movement of hub 54c and needle assembly 40c as described above. Alternatively or in addition thereto, the rearward opening 32c of housing 20c may be closed to prevent access therethrough, thereby safely containing needle assembly 40c therein.

While described herein in terms of specific embodiments, the blood collection device of the present invention generally provides an assembly for effecting blood collection during a normal phlebotomy procedure and for safely containing a used needle after such a procedure in a self-contained device. The simple operation of the device relies on the forces of gravity based on the weight of the needle assembly to retract the used needle assembly within the needle holder upon activation of a simple retainer mechanism which releases the needle. In this manner, the user need only activate the device while in an upright position, which allows for gravitational forces to pull the needle within the needle holder, which then acts as a vessel for safe containment of the used needle. Moreover, the needle is safely maintained within the vessel, such as through a retaining mechanism which ensures that the non-patient end of the needle does not extend through the rear opening of the device. Thus, safe containment is effected within its own assembly, without any complex retraction mechanisms to effect a retractive force, such as springs, which can lose their retractive forces over time. The entire assembly after safety containment of the needle within the needle holder can be appropriately discarded in a conventional medical waste container if desired, or in a sharps container, if preferred.

While satisfied by embodiments in many different forms, specific embodiments are shown in the drawings and described above detail, with the understanding that the present disclosure is to be considered as examplary and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A safety blood collection device comprising:
   a holder housing comprising a generally tubular wall extending between a forward end and an open rearward end to define an interior chamber therein, the rearward end of the holder housing adapted to receive a sample collection tube therethrough;
   a needle including a first end having a patient puncture tip and a second end having a non-patient puncture tip; and
   a retainer or a needle carrier co-acting with the holder housing and adapted to maintain the needle in a first position with the first end extending from the forward end of the holder housing, the retainer or the needle carrier adapted for activation so as to release the needle, such that when the device is in an upright position, the force of gravity is the sole force which acts based on the weight of the needle to move the needle from the first position extending from the forward end of the holder housing to a second position in which the first end is contained within the interior chamber of the holder housing, wherein the retainer or the needle carrier is configured to have a length which is at least equal to or greater than a length of the second end of the needle and wherein movement of the retainer or the needle carrier from the first position toward the second position causes the first end and the second end of the needle to be automatically contained within the interior chamber of the holder housing without further action by an operator.

2. A safety blood collection device as in claim 1, wherein the retainer comprises structure for establishing interference engagement for maintaining the needle in the first position with the patient puncture tip extending from the forward end of the holder housing, and wherein the retainer is adapted to move from a first retainer position to a second retainer position upon activation thereof, movement of the retainer from the first retainer position to the second retainer position causing release of the interference engagement, thereby permitting the needle to move to the second position in which the patient puncture tip is contained within the interior chamber of the holder housing.

3. A safety blood collection device as in claim 2, wherein the retainer comprises a flexible band member including a first portion comprising a slot adjacent the forward end of the holder housing when the flexible band member is in the first retainer position, wherein interference engagement with the slot maintains the needle in the first position with the patient puncture tip extending from the forward end of the holder housing, and wherein movement of the flexible band member toward the second retainer position aligns the needle with a second portion of the flexible band member comprising an opening, thereby releasing the interference engagement and permitting the needle to pass through the opening to the second position in which the patient puncture tip of the needle is contained within the interior chamber of the holder housing.

4. A safety blood collection device as in claim 3, wherein the flexible band member comprises a continuous band member movable about an interior perimeter of the holder housing.

5. A safety blood collection device as in claim 4, further comprising a holder insert contained within the holder housing, the flexible band member sandwiched between the holder insert and the holder housing for movement therebetween.

6. A safety blood collection device as in claim 3, wherein the flexible band member further includes a third portion adapted to enclose the forward end of the holder housing when the flexible band member is in the second retainer position to prevent re-exposure of the patient puncture tip of the needle cannula therethrough.

7. A safety blood collection device as in claim 3, wherein the flexible band member includes a finger tab extending through a portion of the housing for causing movement of the flexible band member from the first retainer position to the second retainer position.

8. A safety blood collection device as in claim 3, wherein the flexible band member includes an opening adjacent the rearward end of the holder housing when the flexible band member is in the first retainer position, and wherein the flexible band member further includes a portion adapted to close the rearward end of the holder housing when the flexible band member is in the second retainer position to prevent access to the interior chamber through the rearward end.

9. A safety blood collection device as in claim 2, wherein the needle comprises a needle hub and the needle includes the patient puncture tip at a forward end thereof with the needle hub interconnected with a hub port adjacent the forward end of the holder housing, wherein the retainer structure is in interference engagement with the hub port to retain the hub port from release from the forward end of the housing and to maintain the needle in the first position, and wherein movement of the retainer to the second retainer position releases the interference engagement between the retainer structure and the hub port, thereby permitting the needle to move to the second position.

10. A safety blood collection device as in claim 2, further comprising structure adapted to close the rearward end of the holder housing when the retainer is in the second retainer position to prevent access to the interior chamber through the rearward end.

11. A safety blood collection device as in claim 1, wherein the needle carrier comprises a ring structure rotatable with respect to the holder housing about a longitudinal axis between a first retainer position and a second retainer position, the ring structure including a finger in interference engagement with the needle for maintaining the needle in the first position extending from the forward end of the holder housing when the ring structure is in the first retainer position, and wherein rotation of the ring structure to the second retainer position releases the interference engagement between the finger and the needle, thereby permitting the needle to move based on the force of gravity to the second position in which the patient puncture tip of the needle is contained within the interior chamber of the holder housing.

12. A safety blood collection device as in claim 11, wherein the ring structure extends about an external surface of the holder housing and includes at least one finger extending through the holder housing for interference engagement with the needle.

13. A safety blood collection device as in claim 12, wherein the needle comprises a needle hub wherein the first end of the needle includes the patient puncture tip at a forward end thereof, the needle hub including at least one gap extending about a periphery thereof, and wherein rotation of the ring structure with respect to the holder housing aligns the at least one finger of the ring structure with the at least one gap of the needle hub, thereby releasing the interference engagement between the at least one finger of the needle hub and thereby permitting the needle hub to move to the second position based on the force of gravity.

14. A safety blood collection device as in claim 13, wherein the needle hub further comprises the needle carrier extending within the interior chamber of the holder housing, the needle carrier preventing movement of the needle hub through the rearward end of the holder housing upon movement of the needle hub to the second position based on the force of gravity.

15. A safety blood collection device as in claim 14, wherein the a first end of the needle includes the patient puncture tip extending from a forward end of the needle hub and the second end of the needle includes the non-patient puncture tip extending from a rearward end of the needle hub for engagement with a sample collection tube received through the rearward end of the holder housing with the finger of the ring structure maintaining the needle hub in the first position, the needle carrier extending beyond the length of the non-patient puncture tip within the interior chamber of the holder housing and including structure for interference engagement with a portion of the holder housing when the needle hub is in the second position, thereby preventing the non-patient puncture tip from extending through the rearward opening of the holder housing.

16. A safety blood collection device as in claim 1, wherein the retainer comprises a clamping mechanism integrated with the holder housing, the clamping mechanism adapted to move between a first position in which the clamping mechanism secures the needle in the first position with the puncture tip extending from the forward end of the holder housing to a second position in which the needle is released from the clamping mechanism, thereby permitting the needle to move based on the force of gravity to the second position.

17. A safety blood collection device as in claim 16, wherein the clamping mechanism comprises a pair of claws adjacent the forward end of the holder housing and extending externally of the holder housing, the pair of claws being movable from a first clamping position establishing interference engagement for maintaining the needle in the first position to move to a second release position releasing the interference engagement so as to permit the needle to move based on the force of gravity to the second position.

18. A safety blood collection device as in claim 1, wherein the needle comprises a needle hub and the first end of the needle includes the patient puncture tip extending from a forward end of the hub and the second end of the needle includes including the non-patient puncture tip extending from a rearward end of the hub for engagement with a sample collection tube received through the rearward end of the holder housing with the retainer maintaining the needle in the first position.

19. A safety blood collection device as in claim 1, wherein the needle carrier extends within the interior chamber of the holder housing and is connected with the needle, the needle carrier preventing movement of the needle through the rearward end of the holder housing upon movement of the needle to the second position based on the force of gravity.

20. A safety blood collection device as in claim 1, wherein the needle comprises a needle hub and the first end of the needle includes the patient puncture tip extending from a forward end of the hub and the second end of the needle includes the non-patient puncture tip extending from a rearward end of the hub for engagement with a sample collection tube received through the rearward end of the holder housing with the needle carrier maintaining the needle in the first position, the needle carrier extending beyond the length of the non-patient puncture tip within the interior chamber of the holder housing and including structure for interference engagement with a portion of the holder housing when the needle is in the second position, thereby preventing the non-patient puncture tip from extending through the rearward opening of the holder housing.

21. A safety blood collection device comprising:
a needle extending between a forward end having a patient puncture tip and a rearward end having a non-patient puncture tip; and
a needle holder comprising a generally tubular wall extending between a forward end and an open rearward end to define an interior chamber therein, the holder retaining the needle in a first position in which the patient puncture tip extends through the forward end of the holder with the non-patient puncture tip maintained within the interior chamber, and adapted to release the needle such that when the device is in an upright position, the force of gravity is the sole force which acts based on the weight of the needle to move the needle from the first position to a second position in which the patient puncture tip and the non-patient puncture tip are contained within the interior chamber of the holder,
wherein a retainer or a needle carrier is configured to have a length which is at least equal to or greater than a length of the rearward end of the needle and wherein release of the needle for movement from the first position toward the second position automatically contains the needle within the interior chamber of the holder without further action by an operator.

22. A safety blood collection device as in claim 21, wherein the retainer is adapted to maintain the needle in the first position, the retainer adapted for activation so as to release the needle from the first position to permit movement to the second position.

23. A safety blood collection device as in claim 21, wherein the needle is contained and maintained within the interior of the holder after release and movement of the needle from the first position to the second position by structure covering the open rearward end of the needle holder.

24. A safety blood collection device as in claim 21, wherein the needle is contained and maintained within the interior of the holder after release and movement of the needle from the first position to the second position by the needle carrier preventing movement of the needle through the open rearward end of the needle holder upon movement of the needle to the second position.

\* \* \* \* \*

UNITED STATES PATENT AND TRADEMARK OFFICE
CERTIFICATE OF CORRECTION

PATENT NO. : 9,320,459 B2
APPLICATION NO. : 11/429808
DATED : April 26, 2016
INVENTOR(S) : Chin Sin Fong et al.

Page 1 of 1

It is certified that error appears in the above-identified patent and that said Letters Patent is hereby corrected as shown below:

In the claims

Column 20, Line 58, Claim 15, delete "the a" and insert -- the --

Column 21, Line 27, Claim 18, delete "includes including" and insert -- includes --

Signed and Sealed this
Twenty-sixth Day of July, 2016

Michelle K. Lee
*Director of the United States Patent and Trademark Office*